US012629443B2

(12) United States Patent
Gal et al.

(10) Patent No.: US 12,629,443 B2
(45) Date of Patent: May 19, 2026

(54) SCENT DISPENSER WITH MODULAR DRUM

(71) Applicant: iRoma Scents A.B. Ltd., Herzliya (IL)

(72) Inventors: Avner Gal, Herzliya (IL); Uzi Malimovka, Givat Shmuel (IL)

(73) Assignee: iRoma Scents A.B. Ltd., Herzliya (IL)

( * ) Notice: Subject to any disclaimer, the term of this patent is extended or adjusted under 35 U.S.C. 154(b) by 0 days.

(21) Appl. No.: 19/010,497

(22) Filed: Jan. 6, 2025

(65) Prior Publication Data

US 2025/0222156 A1     Jul. 10, 2025

Related U.S. Application Data

(60) Provisional application No. 63/618,736, filed on Jan. 8, 2024.

(51) Int. Cl.
A61L 9/14 (2006.01)

(52) U.S. Cl.
CPC ............. A61L 9/14 (2013.01); *A61L 2209/11* (2013.01); *A61L 2209/133* (2013.01); *A61L 2209/134* (2013.01)

(58) Field of Classification Search
CPC .. A61L 9/14; A61L 2209/11; A61L 2209/133; A61L 2209/134
See application file for complete search history.

(56) References Cited

U.S. PATENT DOCUMENTS

| | | |
|---|---|---|
| D209,164 S | 11/1967 | Mclarty |
| D213,366 S | 2/1969 | Griffin |
| D218,281 S | 8/1970 | Diener |
| D222,823 S | 1/1972 | Newman |
| D234,120 S | 1/1975 | Cassin |
| 4,126,418 A | 11/1978 | Krasnow |

(Continued)

FOREIGN PATENT DOCUMENTS

| | | |
|---|---|---|
| CN | 210722430 U | 6/2020 |
| CN | 212256887 U | 12/2020 |

(Continued)

OTHER PUBLICATIONS

U.S. Appl. No. 63/618,736, filed Jan. 8, 2024, iRoma Scents A.B. Ltd.

(Continued)

*Primary Examiner* — Brendan A Hensel
(74) *Attorney, Agent, or Firm* — M&B IP Analysts, LLC

(57) ABSTRACT

A modular scent dispenser may include a drum with chambers that can be inserted into the drum. The chambers may contain different scent essence fluids in order to disperse different scents, and may include mechanical components such as pumps and actuators in order to effectuate scent dispensing. The drum and chambers may be inserted into a housing, which in turn may include motors and other mechanical components for use in actuating the actuators and rotating the drum in order to enable dispensing scents of choice. The scent dispenser including such drum, chambers, and housing may further include computing components such as a scanner in order to scan machine-readable and writeable tags, which may be utilized to determine positions of compartments in the drum and/or scent essences disposed in chambers.

17 Claims, 30 Drawing Sheets

(56) References Cited

U.S. PATENT DOCUMENTS

| | | | |
|---|---|---|---|
| D277,891 | S | 3/1985 | Uffenheimer et al. |
| D287,633 | S | 1/1987 | Hollar et al. |
| D287,634 | S | 1/1987 | Carr et al. |
| 4,956,148 | A | 9/1990 | Grandone |
| D319,650 | S | 9/1991 | Hart |
| D321,057 | S | 10/1991 | Holen |
| D337,387 | S | 7/1993 | Frenkel et al. |
| D338,522 | S | 8/1993 | Muderlak |
| D359,128 | S | 6/1995 | Kesling |
| D363,981 | S | 11/1995 | Muderlak |
| D404,478 | S | 1/1999 | Muderlak |
| D432,407 | S | 10/2000 | Lee |
| D433,130 | S | 10/2000 | Cude et al. |
| D455,774 | S | 4/2002 | Senda et al. |
| D459,651 | S | 7/2002 | Gagnon |
| D507,174 | S | 7/2005 | Katz et al. |
| D511,688 | S | 11/2005 | Baron |
| D531,049 | S | 10/2006 | De France |
| D533,931 | S | 12/2006 | Miller et al. |
| 7,387,265 | B2 | 6/2008 | Hess et al. |
| D579,343 | S | 10/2008 | Calvo |
| 7,610,118 | B2 | 10/2009 | Schramm et al. |
| D616,017 | S | 5/2010 | Partridge, Jr. |
| D628,489 | S | 12/2010 | Caten et al. |
| 7,942,388 | B2 | 5/2011 | Suissa et al. |
| D640,362 | S | 6/2011 | Boshuizen et al. |
| D646,579 | S | 10/2011 | Rahe |
| 8,170,405 | B2 | 5/2012 | Harris |
| D675,529 | S | 2/2013 | Jacobs et al. |
| D720,704 | S | 1/2015 | Yamanaka |
| D721,591 | S | 1/2015 | Hefetz et al. |
| D741,723 | S | 10/2015 | Staab |
| D743,651 | S | 11/2015 | Hoffman |
| D745,522 | S | 12/2015 | York et al. |
| 9,229,311 | B2 | 1/2016 | Yeremian |
| D754,785 | S | 4/2016 | Gibson et al. |
| 9,352,065 | B2 | 5/2016 | Habbel |
| D759,502 | S | 6/2016 | McGregor |
| D802,429 | S | 11/2017 | Williams |
| 10,064,970 | B1 * | 9/2018 | Shah ...................... A61L 9/125 |
| D842,121 | S | 3/2019 | Lee |
| D854,506 | S | 7/2019 | Krishnan et al. |
| 10,814,028 | B2 | 10/2020 | Becker et al. |
| D924,691 | S | 7/2021 | Dalton |
| 11,298,503 | B2 | 4/2022 | Baniasadi et al. |
| D961,397 | S | 8/2022 | Pinson |
| D1,005,113 | S | 11/2023 | Ericson |
| D1,030,484 | S | 6/2024 | Gal et al. |
| D1,042,882 | S | 9/2024 | Gal et al. |
| D1,074,448 | S | 5/2025 | Li |
| 2005/0150366 | A1 | 7/2005 | Susami |
| 2008/0257978 | A1 | 10/2008 | Marth et al. |
| 2011/0200488 | A1 | 8/2011 | Cennini et al. |
| 2014/0001286 | A1 * | 1/2014 | Scott ...................... A61L 9/125 239/303 |
| 2015/0027301 | A1 | 1/2015 | Shih et al. |
| 2016/0107186 | A1 | 4/2016 | Chao et al. |
| 2017/0216474 | A1 * | 8/2017 | Kelsen ................... A61L 9/125 |
| 2018/0369442 | A1 | 12/2018 | Kelsen |
| 2019/0160195 | A1 | 5/2019 | Kelsen |
| 2020/0078485 | A1 | 3/2020 | Suarez Iribarne et al. |
| 2020/0276353 | A1 * | 9/2020 | Juving-Brunet ........ A61L 9/122 |
| 2021/0138099 | A1 * | 5/2021 | Andrews ................ A61L 2/202 |
| 2021/0170060 | A1 * | 6/2021 | Galvão ................... A61L 9/14 |
| 2023/0285623 | A1 | 9/2023 | Jones et al. |

FOREIGN PATENT DOCUMENTS

| | | |
|---|---|---|
| CN | 213583088 U | 6/2021 |
| EP | 1837860 A2 | 9/2007 |
| IL | 70713 A | 9/1989 |
| JP | 2004198657 A | 7/2004 |
| JP | 2007249141 A | 9/2007 |
| JP | 2007249140 B | 4/2011 |
| JP | 2018036642 A | 3/2018 |
| KR | 101173541 B1 | 8/2012 |
| WO | 2008098939 A1 | 8/2008 |
| WO | 2009006851 A1 | 1/2009 |
| WO | 2011021980 A1 | 2/2011 |
| WO | 2018108584 A1 | 6/2018 |
| WO | 2019114312 A1 | 6/2019 |
| WO | D228299002 | 4/2023 |
| WO | 2023119275 A1 | 6/2023 |
| WO | 237331 | 6/2024 |

OTHER PUBLICATIONS

International Search Report for PCT/IB2024/058056, dated Oct. 31, 2024. Searching Authority, Israel Patent Office, Jerusalem, Israel.

International Search Report for PCT/IL2022/051351, dated Mar. 29, 2023. International Searching Authority Israel Patent Office Jerusalem, Israel.

Written Opinion of the International Searching Authority for PCT/IL2022/051351, dated Mar. 29, 2023. International Searching Authority Israel Patent Office Jerusalem, Israel.

Written Opinion of the Searching Authority for PCT/IB2024/058056, dated Oct. 31, 2024. Searching Authority, Israel Patent Office, Jerusalem, Israel.

International Search Report for PCT/IB2025/050126, dated Apr. 3, 2025. Searching Authority, Israel Patent Office, Jerusalem, Israel.

Written Opinion of the Searching Authority for PCT/IB2025/050126, dated Apr. 3, 2025. Searching Authority, Israel Patent Office, Jerusalem, Israel.

* cited by examiner

SCENT DISPENSER WITH MODULAR DRUM

CROSS-REFERENCE TO RELATED APPLICATIONS

This application claims the benefit of U.S. Provisional Patent Application No. 63/618,736 filed on Jan. 8, 2024, the contents of which are hereby incorporated by reference.

TECHNICAL FIELD

The present disclosure relates generally to scent dispensing and, more specifically, to scent dispensers with interchangeable scent chambers.

BACKGROUND

Scent dispensers are devices designed to emit scents through one or more mechanisms. For example, scent dispensers may cause projection of fluids of particular scents or combinations of scents in order to emulate the effects of smelling items having certain scents.

As part of the scent dispensing experience, users may wish to customize their experience. Some existing solutions allow for changing the scent fluid, thereby allowing for dispensing other scents. Other techniques and devices which allow for further customization, and particularly more flexibility in customizing, would be desirable.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include an assembly. The assembly comprises: a housing; a platform disposed in the housing; a drum disposed on the platform, the drum having a tray defining a plurality of compartments, wherein at least one first compartment of the plurality of compartments is adapted to receive a respective chamber of a plurality of chambers; a first motor, wherein the first motor is connected to the platform; a second motor, wherein the second motor is adapted to connect to a plurality of actuators of the plurality of chambers; and a controller communicatively connected to the motor, the controller including a processing circuitry and a memory, wherein the controller is configured to provide a first set of input signals to the first motor in order to cause the first motor to engage the drum, wherein the platform rotates when engaged by the first motor, wherein the controller is further configured to provide a second set of input signals to the second motor in order to cause the second motor to engage actuators among the plurality of actuators.

Certain embodiments disclosed herein include the assembly as noted above or below, further comprising: the plurality of chambers, wherein each chamber of the plurality of chambers is disposed in a compartment of the plurality of compartments, wherein each chamber of the plurality of chambers includes a casing defining a cavity adapted to store a respective fluid of a plurality of fluids.

Certain embodiments disclosed herein include the assembly as noted above or below, wherein each chamber of the plurality of chambers includes a nozzle connected to a pump, wherein the pump of each chamber is in fluid connection with the cavity of the chamber, wherein fluid in the cavity of each chamber is ejected from the cavity and exits the chamber through the nozzle of the chamber when force is exerted on the pump of the chamber.

Certain embodiments disclosed herein include the assembly as noted above or below, wherein the pump of each chamber includes a respective actuator of the plurality of actuators that is in fluid connection with the cavity of the chamber such that movement by the actuator of the pump of the chamber exerts force on the fluid in the cavity of the chamber.

Certain embodiments disclosed herein include the assembly as noted above or below, wherein the actuator of the pump of each chamber has a top portion defining a slot and a fin disposed in the slot defined in the top portion.

Certain embodiments disclosed herein include the assembly as noted above or below, wherein each chamber of the plurality of chambers further includes a valve, wherein the valve of each chamber is fluidly connected to the cavity of the chamber.

Certain embodiments disclosed herein include the assembly as noted above or below, wherein the tray defines a plurality of holes, wherein the casing of each cavity further includes a snap member, wherein the snap member of each chamber is configured to lock into one of the plurality of holes of the tray in order to lock the chamber in place within the tray.

Certain embodiments disclosed herein include the assembly as noted above or below, wherein each chamber has a machine-readable marker disposed thereon, further comprising: a scanner, wherein the scanner is configured to scan the machine-readable marker disposed on each chamber, wherein the controller is further configured to determine a scent essence of each chamber by scanning the machine-readable marker disposed on the chamber.

Certain embodiments disclosed herein include the assembly as noted above or below, wherein the casing of each chamber defines a depression adapted to receive a machine-readable tag of a plurality of machine-readable tags, further comprising: a scanner, wherein the scanner is configured to scan the plurality of machine-readable markers, wherein the controller is further configured to determine a scent essence of each chamber by scanning the plurality of machine-readable markers.

Certain embodiments disclosed herein include the assembly as noted above or below, wherein the casing of each chamber further includes a first portion and a second portion, wherein the cavity of each chamber is defined in the first portion of the chamber, wherein the first portion of each chamber has a top side, wherein the second portion of each chamber extends from the top side of the first portion of the chamber.

Certain embodiments disclosed herein include the assembly as noted above or below, wherein the second portion of the casing of each chamber has a first curved wall and a second curved wall.

Certain embodiments disclosed herein include the assembly as noted above or below, wherein the controller is further configured to: determine an orientation of the plurality of chambers with respect to the aperture of the housing; cause rotation of the tray until a first chamber of the plurality of chambers is aligned with the aperture of the housing; and cause fluid to be dispensed from the first chamber through the aperture of the housing by providing the input signals to the motor when the first chamber is aligned with the aperture of the housing.

Certain embodiments disclosed herein include the assembly as noted above or below, wherein the plurality of compartments includes the at least one first compartment and a second compartment, wherein each of the at least one first compartment has a bottom end defining at least one aperture, wherein the second compartment has a bottom end which lacks an aperture.

Certain embodiments disclosed herein include the assembly as noted above or below, wherein the second compartment has a machine-readable marker disposed thereon, further comprising: a scanner, wherein the scanner is configured to scan the machine-readable marker disposed on the second compartment, wherein the controller is further configured to determine a type of the drum by scanning the machine-readable marker disposed on the second compartment.

Certain embodiments disclosed herein include the assembly as noted above or below, wherein the plurality of compartments includes the at least one first compartment and a second compartment, the second compartment has a set of side walls and at least one rib, wherein each rib is disposed on one of the side walls of the set of side walls.

Certain embodiments disclosed herein include a method for dispensing scents. The method comprises: causing a drum to rotate until a first chamber of a plurality of chambers is aligned with an aperture defined in the housing by providing a first set of input signals to a first motor of an assembly; wherein the assembly includes a housing defining the aperture, a platform disposed in the housing, a drum disposed on the platform, the first motor, a second motor, and the plurality of chambers; wherein the drum has a tray defining a plurality of compartments; wherein each chamber of the plurality of chambers is disposed in a compartment of the plurality of compartments; wherein each chamber of the plurality of chambers includes a casing defining a cavity adapted to store a respective fluid of a plurality of fluids; wherein each chamber of the plurality of chambers further includes a nozzle connected to a pump; wherein the pump of each chamber includes a respective actuator of a plurality of actuators; wherein the pump of each chamber is in fluid connection with the cavity of the chamber; and causing the actuator of the pump of the first chamber of the plurality of chambers to exert force on the pump of the first chamber when the first chamber is aligned with the aperture defined in the housing by providing a second set of input signals to the second motor; wherein the second motor is connected to the plurality of actuators of the plurality of chambers; wherein fluid in the cavity of each chamber is ejected from the cavity and exits the chamber through the nozzle of the chamber when force is exerted on the pump of the chamber.

Certain embodiments disclosed herein also include a non-transitory computer-readable medium having stored thereon causing a processing circuitry to execute a process, the process comprising: causing a drum to rotate until a first chamber of a plurality of chambers is aligned with an aperture defined in the housing by providing a first set of input signals to a first motor of an assembly; wherein the assembly includes a housing defining the aperture, a platform disposed in the housing, a drum disposed on the platform, the first motor, a second motor, and the plurality of chambers; wherein the drum has a tray defining a plurality of compartments; wherein each chamber of the plurality of chambers is disposed in a compartment of the plurality of compartments; wherein each chamber of the plurality of chambers includes a casing defining a cavity adapted to store a respective fluid of a plurality of fluids; wherein each chamber of the plurality of chambers further includes a nozzle connected to a pump; wherein the pump of each chamber includes a respective actuator of a plurality of actuators; wherein the pump of each chamber is in fluid connection with the cavity of the chamber; and causing the actuator of the pump of the first chamber of the plurality of chambers to exert force on the pump of the first chamber when the first chamber is aligned with the aperture defined in the housing by providing a second set of input signals to the second motor; wherein the second motor is connected to the plurality of actuators of the plurality of chambers; wherein fluid in the cavity of each chamber is ejected from the cavity and exits the chamber through the nozzle of the chamber when force is exerted on the pump of the chamber.

Certain embodiments disclosed herein also include a system for dispensing scents. The system comprises: a processing circuitry; and a memory, the memory containing instructions that, when executed by the processing circuitry, configure the system to: cause a drum to rotate until a first chamber of a plurality of chambers is aligned with an aperture defined in the housing by providing a first set of input signals to a first motor of an assembly; wherein the assembly includes a housing defining the aperture, a platform disposed in the housing, a drum disposed on the platform, the first motor, a second motor, and the plurality of chambers; wherein the drum has a tray defining a plurality of compartments; wherein each chamber of the plurality of chambers is disposed in a compartment of the plurality of compartments; wherein each chamber of the plurality of chambers includes a casing defining a cavity adapted to store a respective fluid of a plurality of fluids; wherein each chamber of the plurality of chambers further includes a nozzle connected to a pump; wherein the pump of each chamber includes a respective actuator of a plurality of actuators; wherein the pump of each chamber is in fluid connection with the cavity of the chamber; and cause the actuator of the pump of the first chamber of the plurality of chambers to exert force on the pump of the first chamber when the first chamber is aligned with the aperture defined in the housing by providing a second set of input signals to the second motor; wherein the second motor is connected to the plurality of actuators of the plurality of chambers; wherein fluid in the cavity of each chamber is ejected from the cavity and exits the chamber through the nozzle of the chamber when force is exerted on the pump of the chamber.

Certain embodiments disclosed herein include a method, non-transitory computer-readable medium, or system as noted above or below, further including or being configured to perform the following step or steps: determining an orientation of the plurality of chambers with respect to the aperture defined in the housing, wherein the drum is caused to rotate based on the determined orientation.

Certain embodiments disclosed herein include a method, non-transitory computer-readable medium, or system as noted above or below, wherein each chamber of the plurality of chambers has a machine-readable marker disposed thereon, further including or being configured to perform the following step or steps: scanning the machine-readable marker of at least one chamber of the plurality of chambers, wherein the orientation is determined based on the scanning.

Certain embodiments disclosed herein include a method, non-transitory computer-readable medium, or system as noted above or below, wherein the plurality of compartments includes at least one first compartment and a second compartment, wherein the second compartment has a machine-readable marker disposed thereon, further including or being configured to perform the following step or steps: scanning the machine-readable marker disposed on the second compartment; determining a type of the drum based on the scanning of the machine-readable marker disposed on the second compartment, wherein the drum is caused to rotate based on the determined type of the drum.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

6

Figure 10:
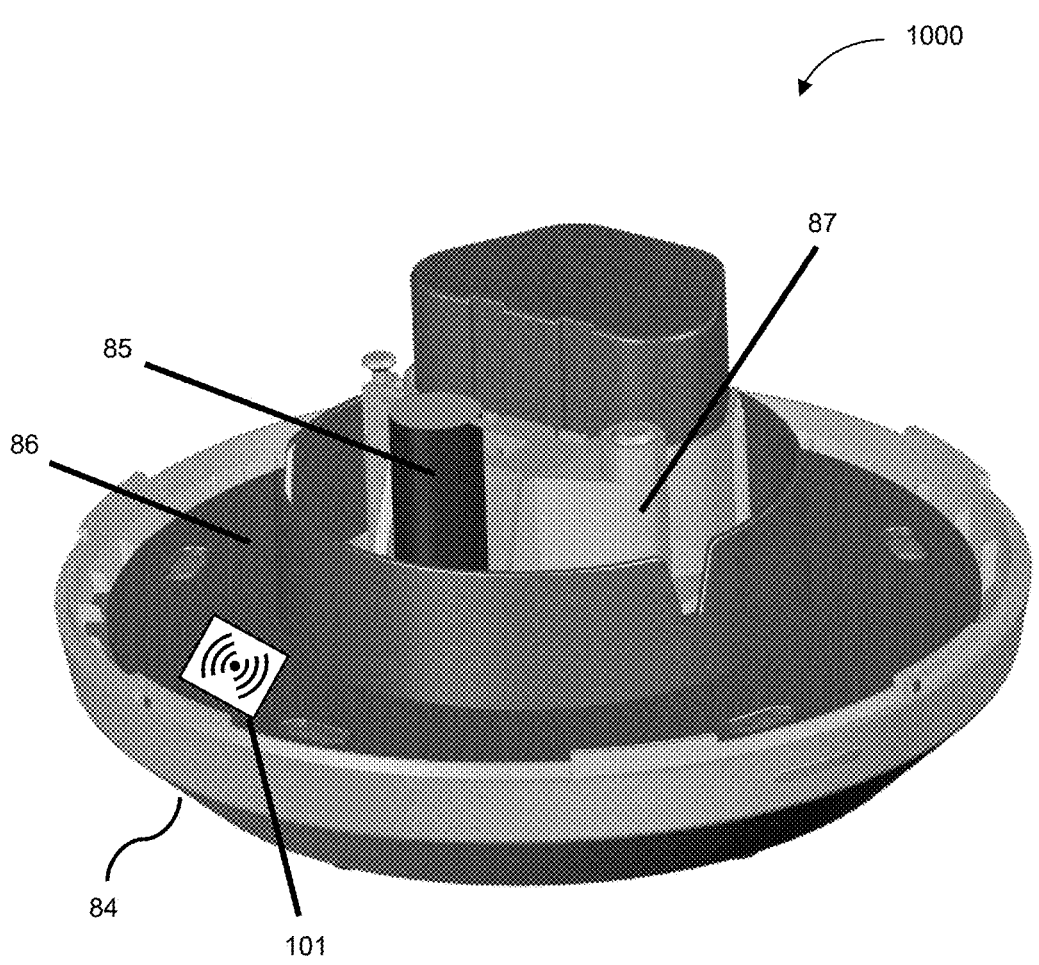

FIG. 10 is an illustration of a bottom portion of a scent dispenser assembly demonstrating components utilized for causing movement of the actuators which may be utilized in accordance with various disclosed embodiments.

Figure 11A:
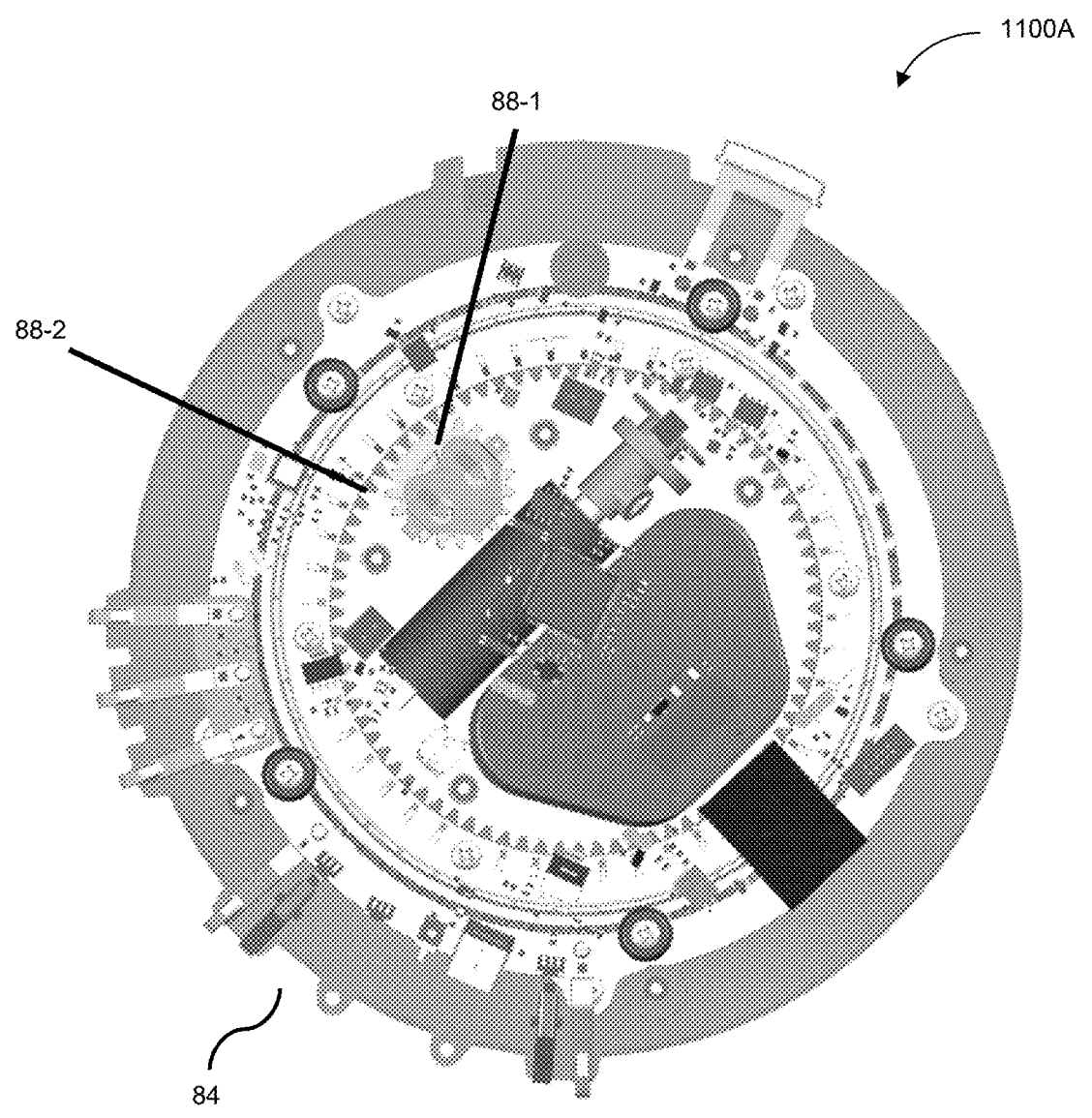

FIG. 11A is a bottom interior view which may be utilized in accordance with various disclosed embodiments.

Figure 11B:
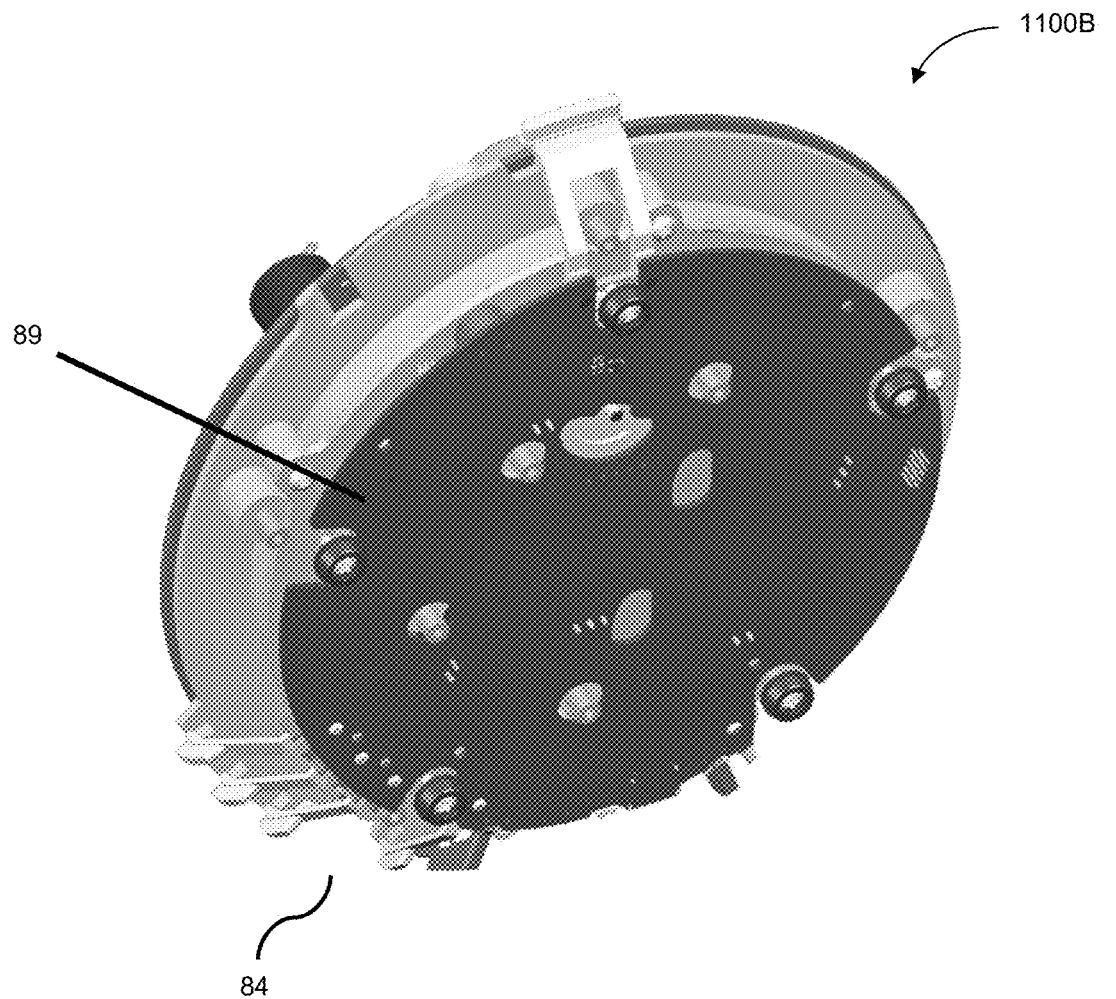

FIG. 11B is a bottom interior view showing placement of a printed circuit board (PCB) on the bottom portion which may be utilized in accordance with various disclosed embodiments.

Figure 12:
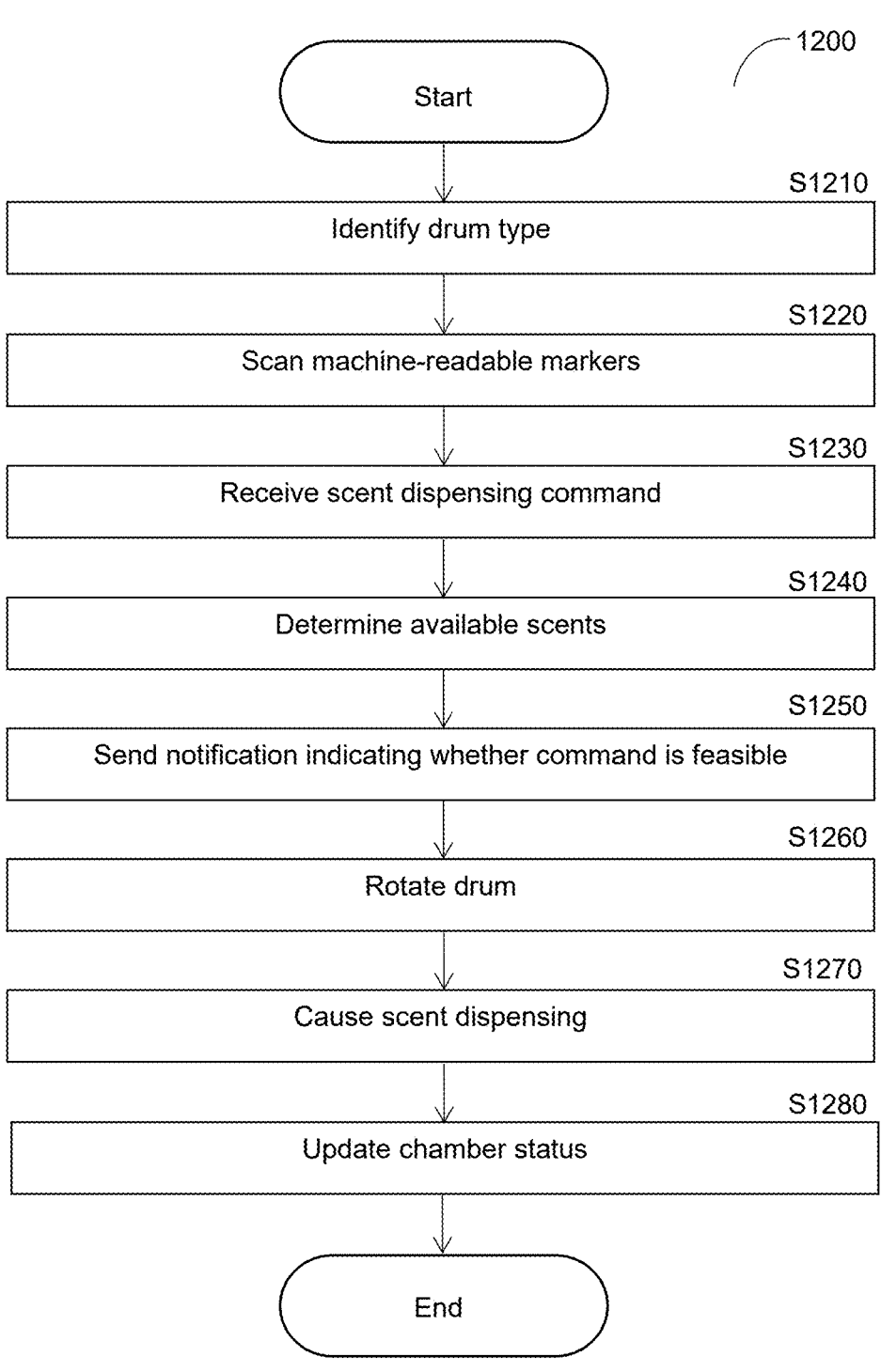

FIG. 12 is a flowchart illustrating a method for dispensing scent using orientation detection with respect to a modular scent dispenser according to an embodiment.

Figure 13:
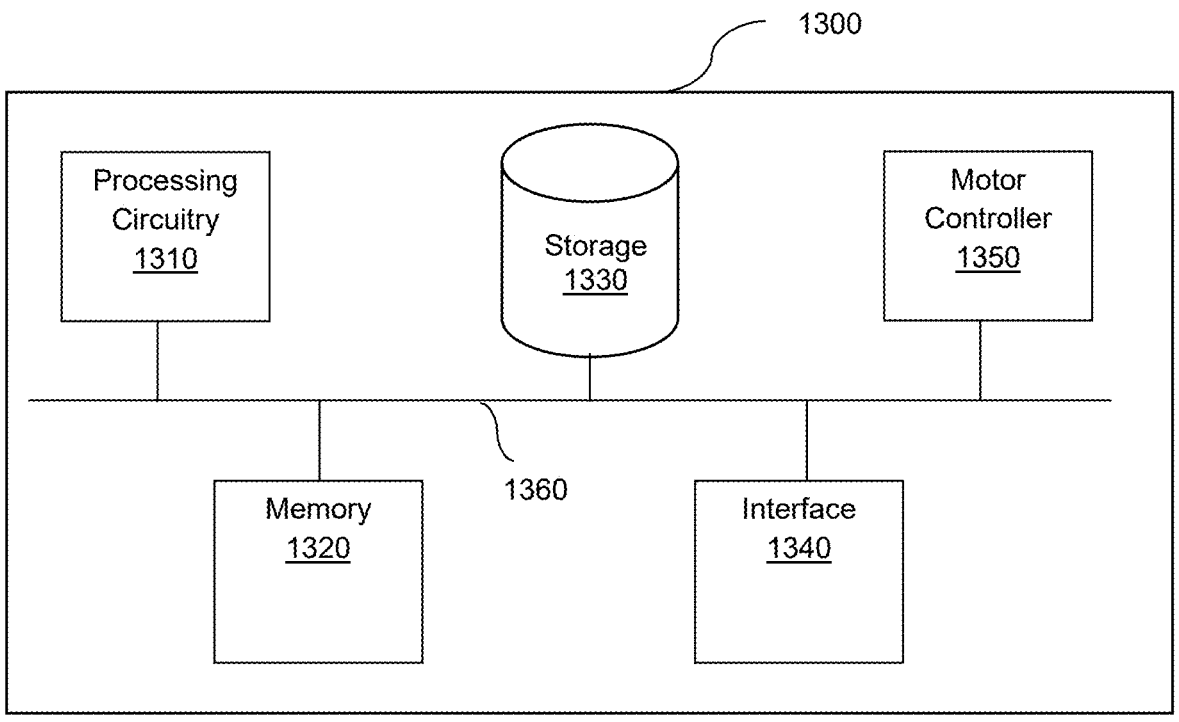

FIG. 13 is a schematic diagram of a hardware layer of a system configured to control scent dispensing of a modular scent dispenser according to an embodiment.

Figure 14:
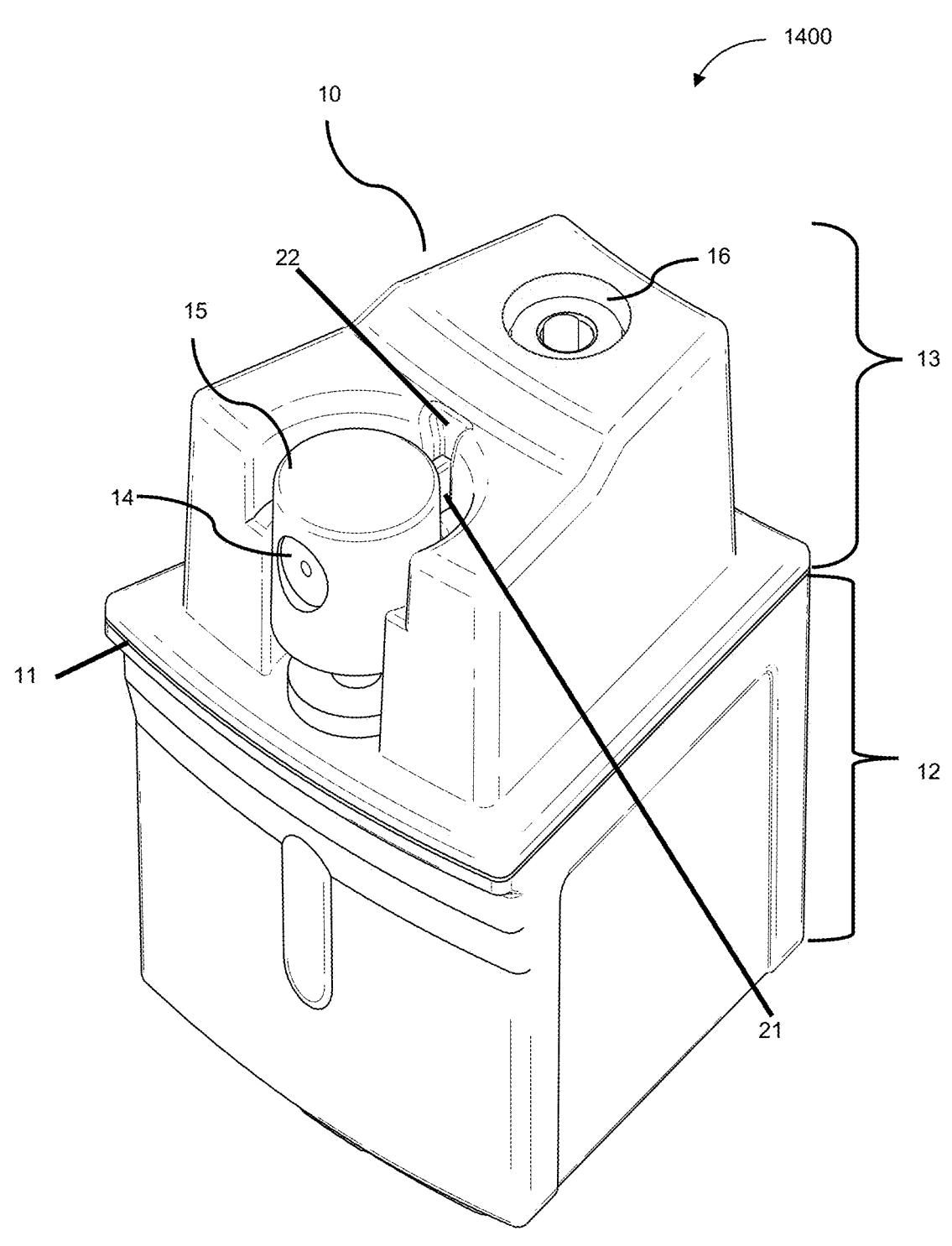

FIG. 14 is a top perspective view of a chamber according to an embodiment.

Figure 15:
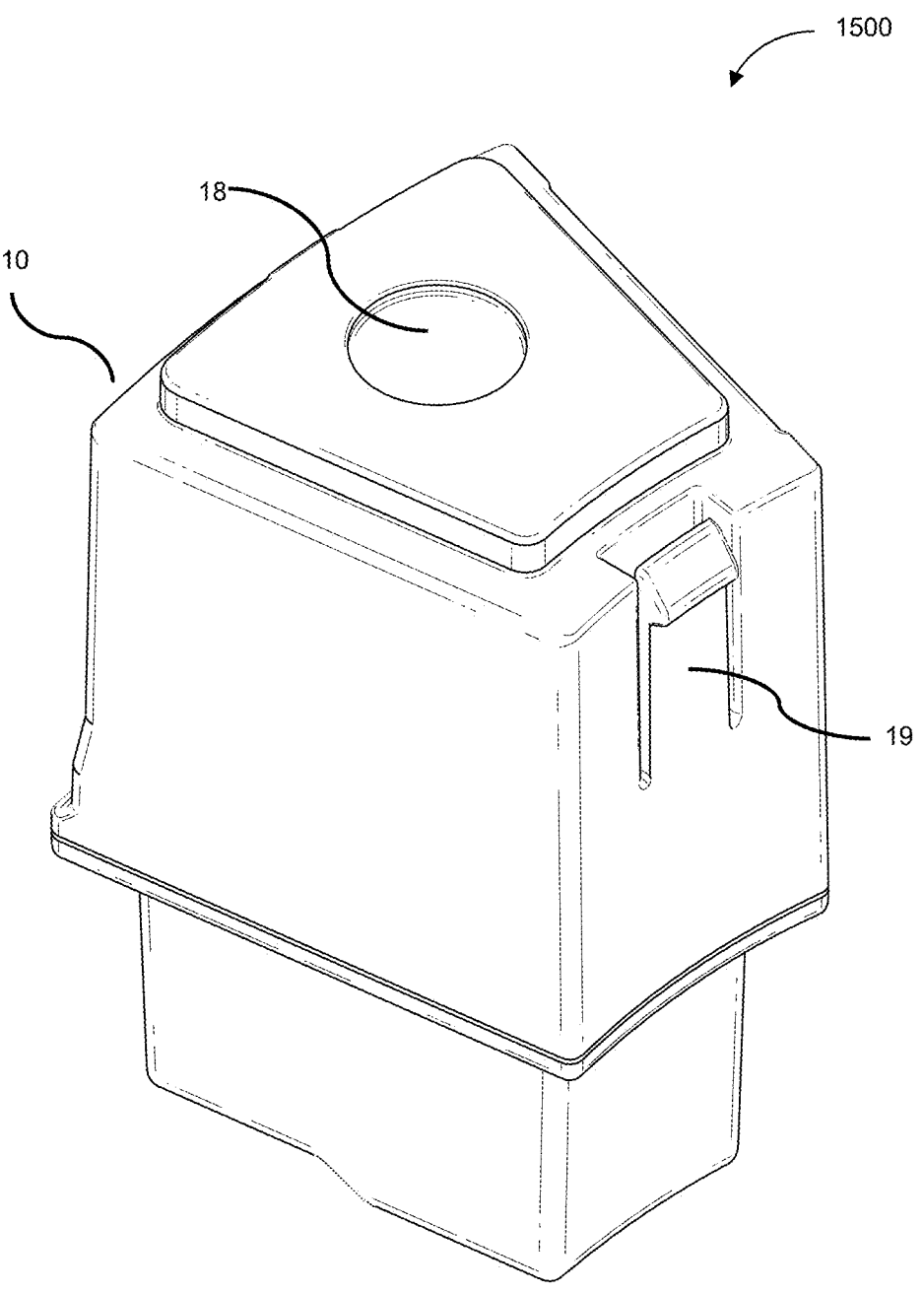

FIG. 15 is a bottom perspective view of a chamber according to an embodiment.

Figure 16:
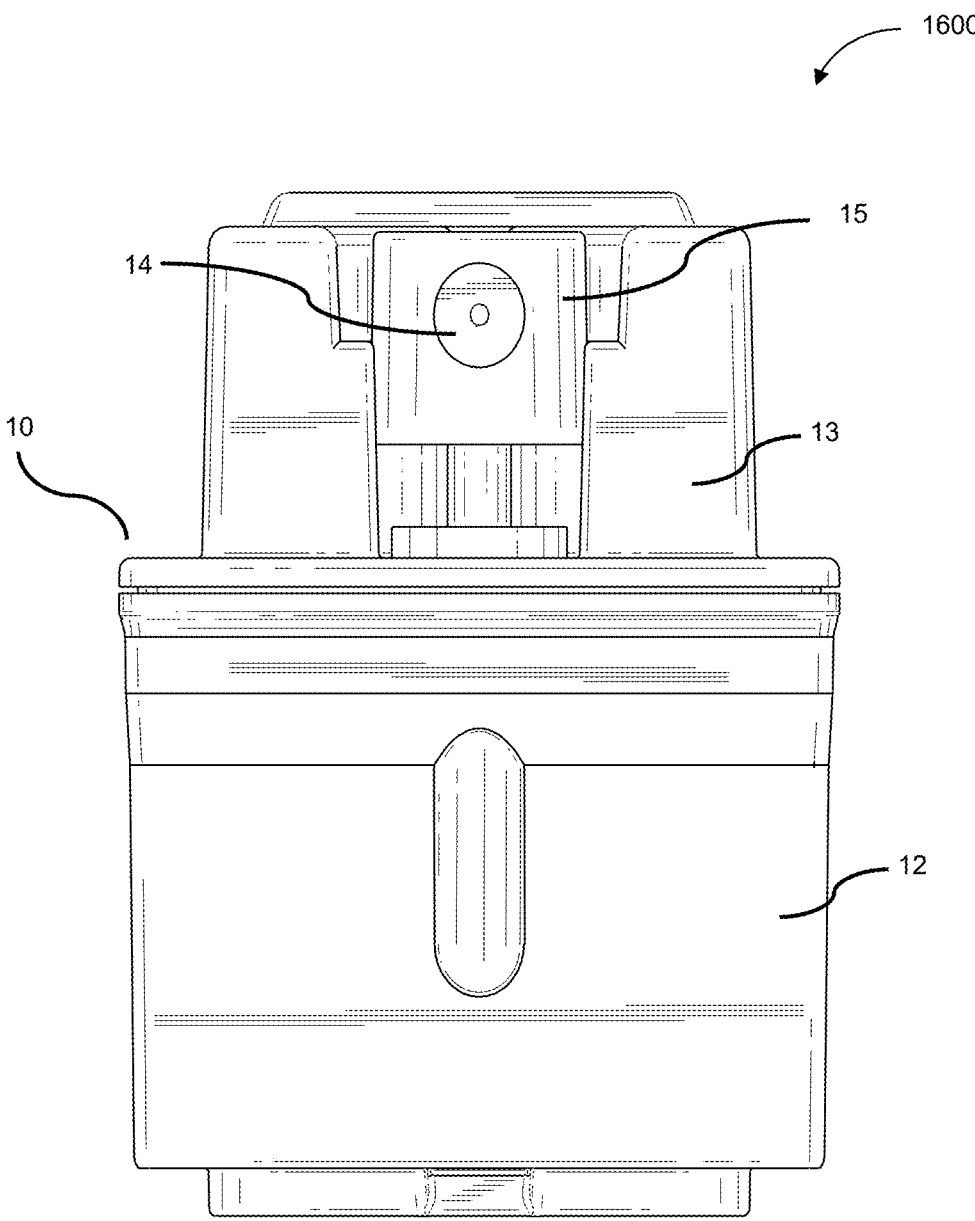

FIG. 16 is a front view of a chamber according to an embodiment.

Figure 17:
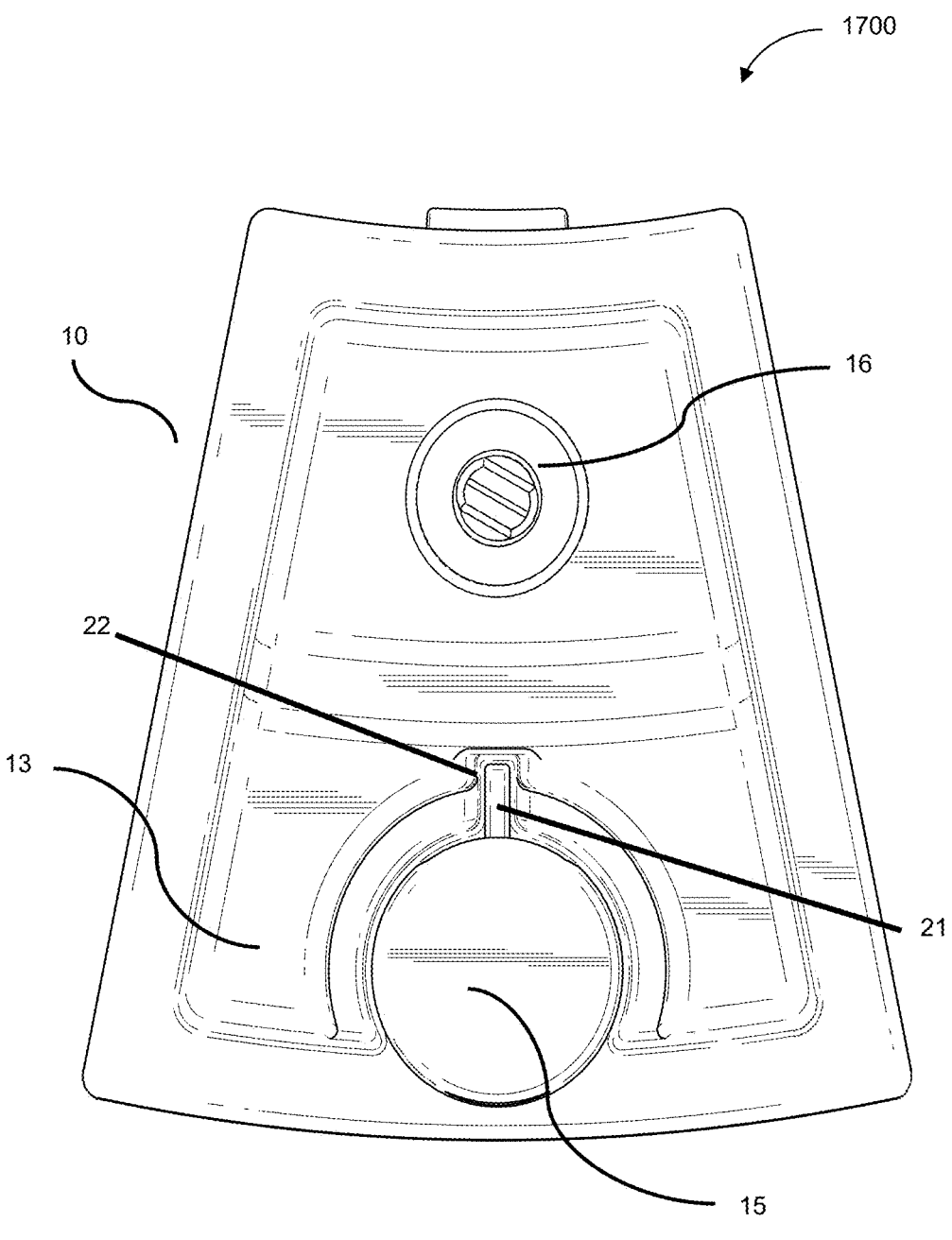

FIG. 17 is a top view of a chamber according to an embodiment.

Figure 18:
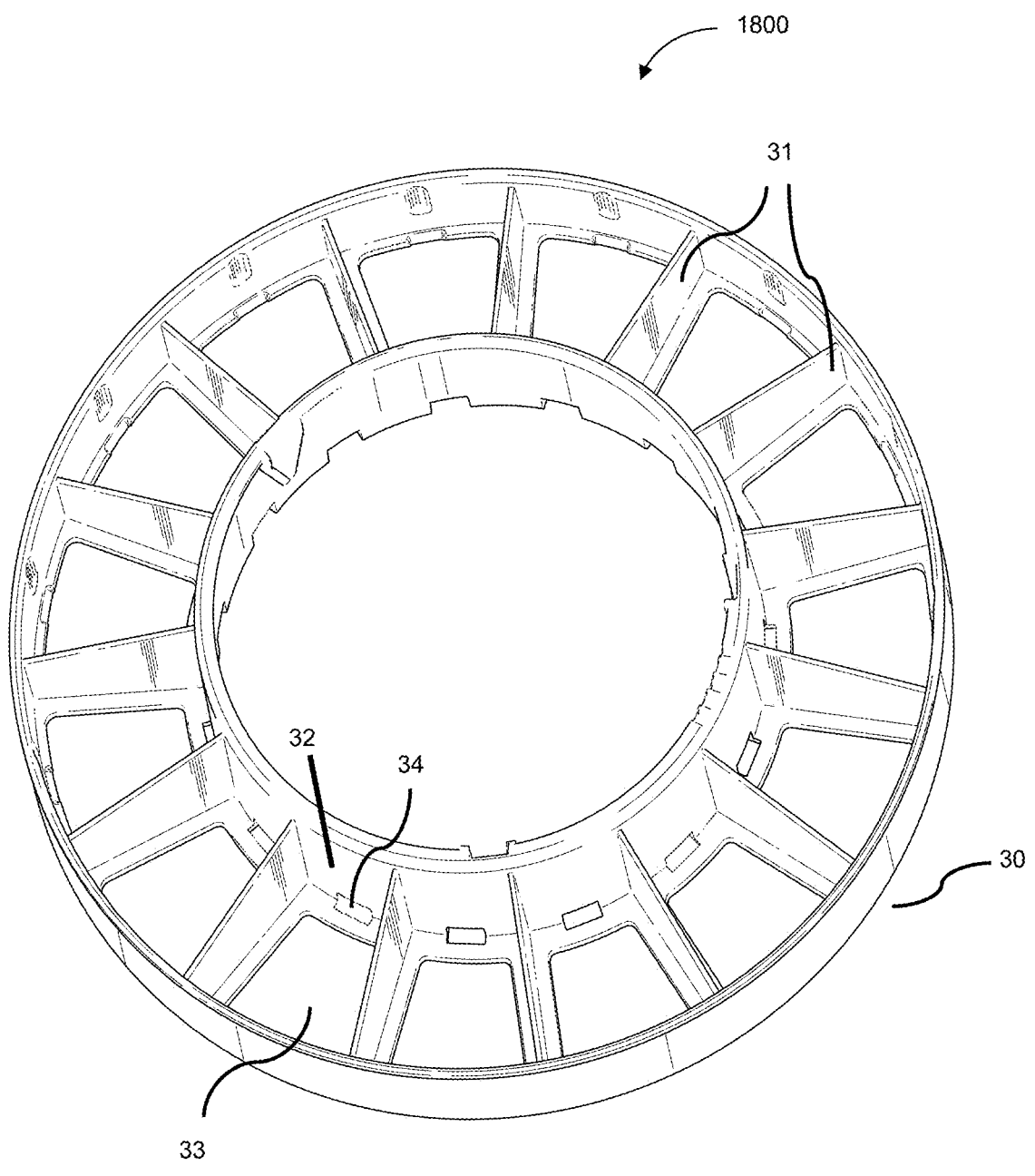

FIG. 18 is a perspective view of a drum according to an embodiment.

Figure 19:
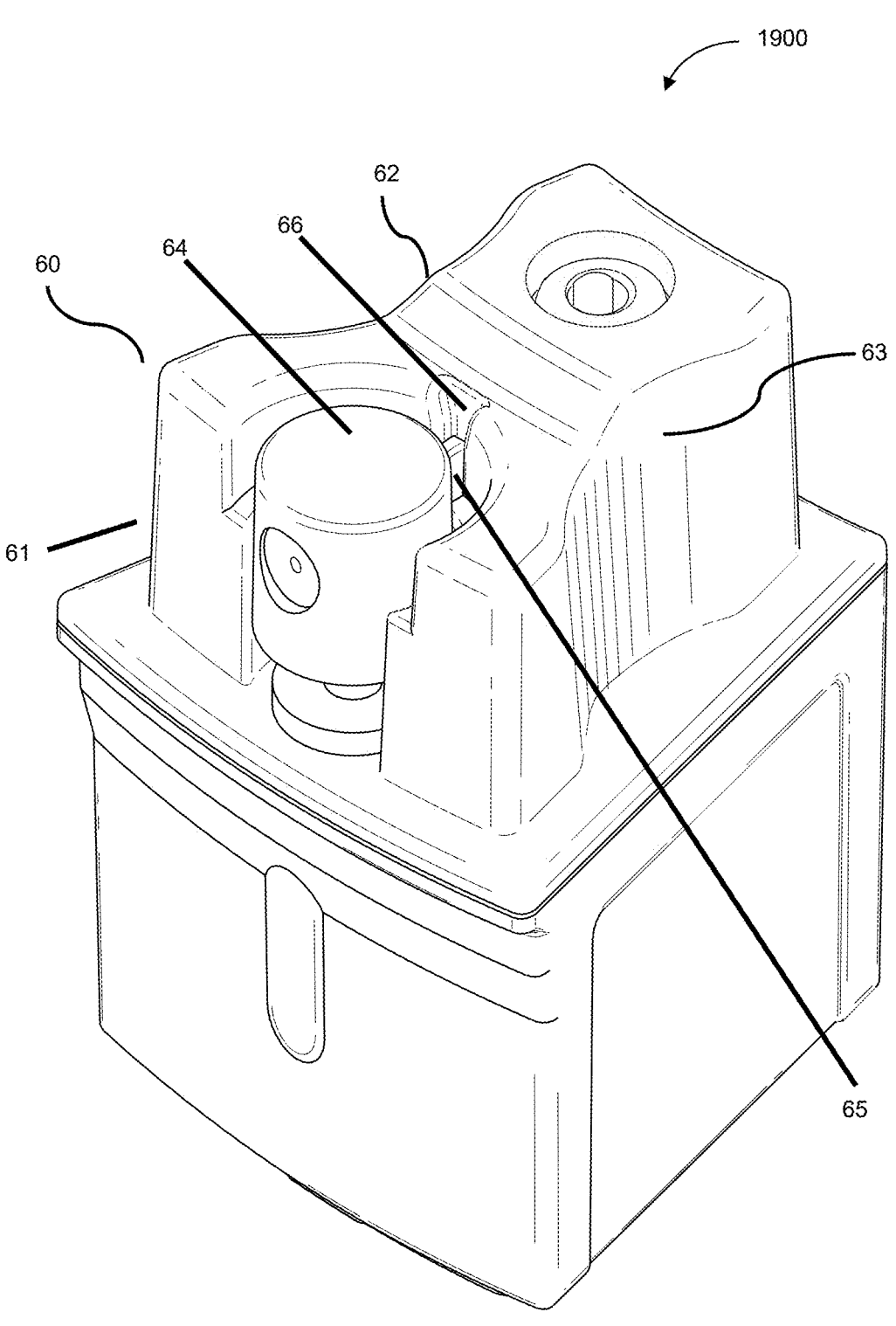

FIG. 19 is a perspective view of a chamber having curved upper walls according to an embodiment.

Figure 20:
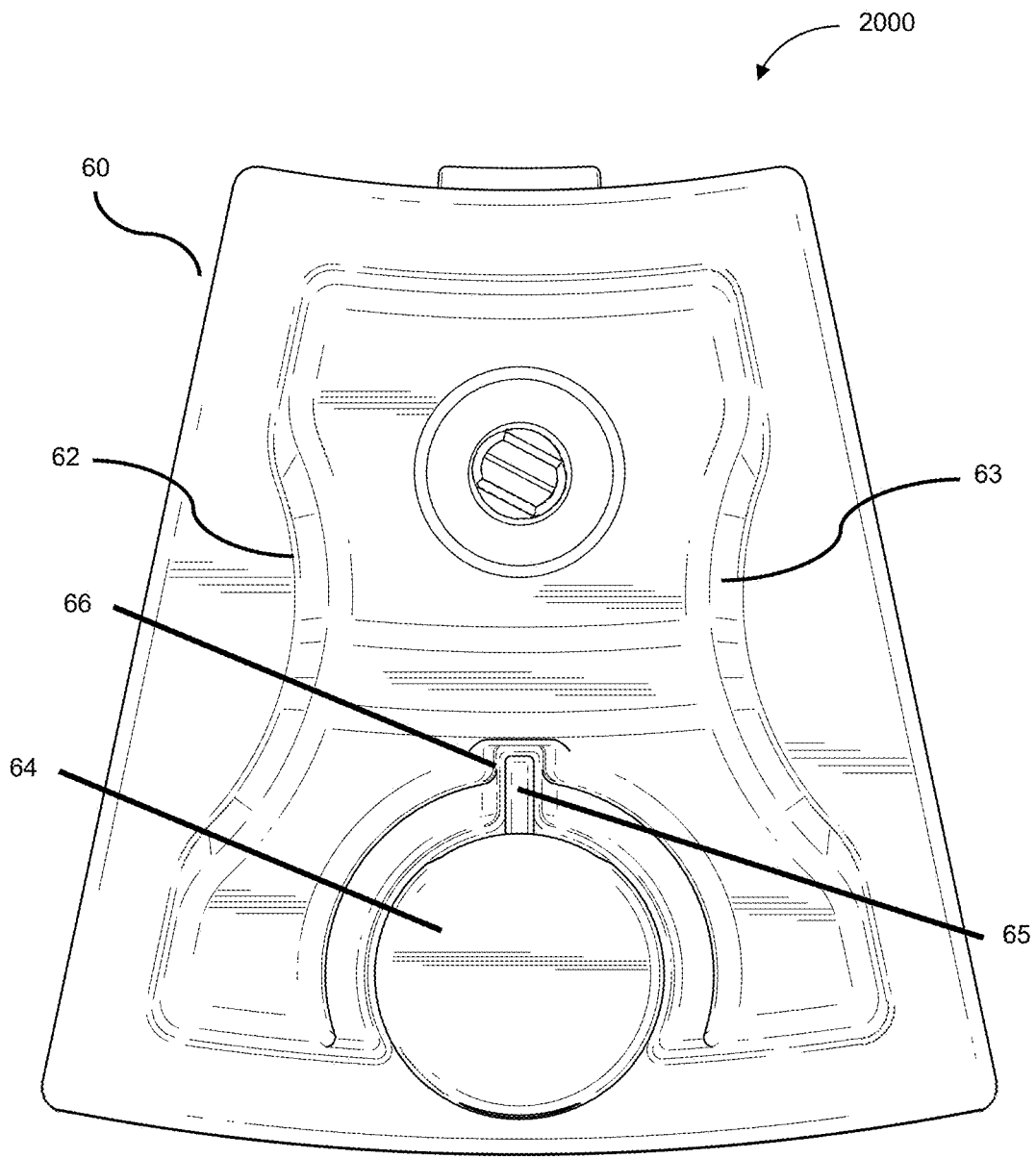

FIG. 20 is a top view of a chamber having curved upper walls according to an embodiment.

Figure 21:
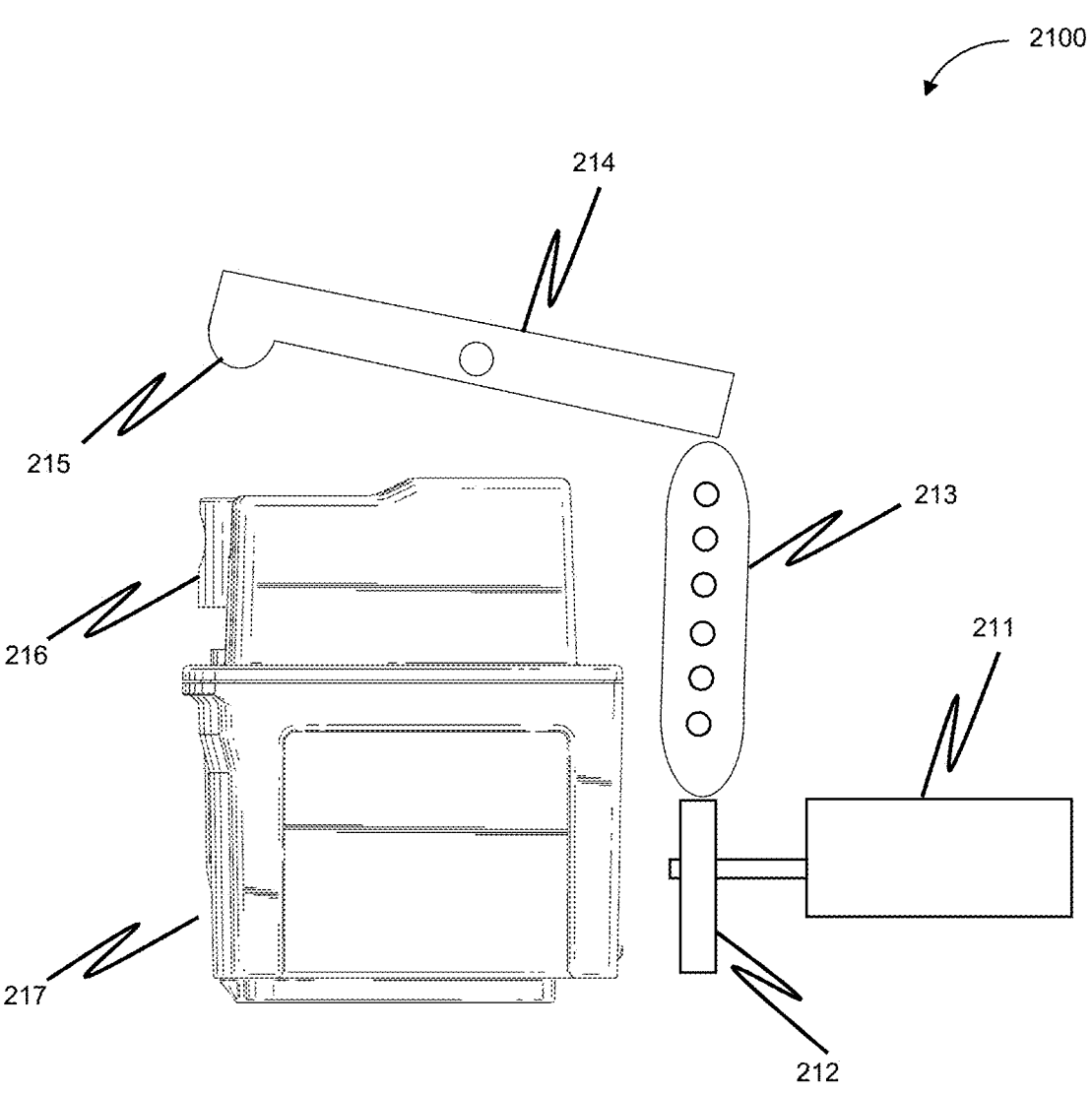

FIG. 21 is an illustration of a mechanism for causing actuators to move which may be utilized in accordance with various disclosed embodiments.

DETAILED DESCRIPTION

The various disclosed embodiments include components and assemblies of modular dispensers. The dispensers disclosed herein may be utilized to dispense liquid or other substances such as, but not limited to, scent essence, other fragrance fluids, or other scent essence materials. Moreover, the dispenser design, in accordance with various disclosed embodiments, is modular at least insofar as certain chambers which may be loaded with fluids can be interchangeably removed and replaced within a drum, thereby allowing for changing the dispensing configuration of the modular dispenser.

In accordance with various disclosed embodiments, the chambers in the modular dispenser may be removed and replaced in order to allow for refilling chambers, to switch chambers containing one fluid with chambers containing a different fluid, both, and the like. In this regard, when utilized for dispensing scents, the chambers in the modular dispenser may be swapped with chambers containing different scent essences in order to provide for different combinations of scent essences, effectively allowing for dispensing different scents.

In an embodiment, a modular scent dispenser includes a drum having a tray with one or more compartments into which chambers may be inserted. Each chamber is configured to receive one or more fluids (e.g., scent essences) or other materials. The chambers are removably disposed in the drum such that they can be swapped out or otherwise replaced with other chambers. The drum and chambers may further be disposed within a housing. The housing, in turn, may define one or more apertures through which scents may be dispensed (e.g., through spraying fluids from the chambers through the aperture via a nozzle of each chamber).

In an embodiment, each chamber includes a nozzle connected to a pump, which in turn is in fluid connection with a cavity in which fluid (e.g., scent essence) may be disposed such that, when force is exerted on the pump, fluid is ejected from the cavity and out of the chamber through the nozzle. To this end, the pump includes an actuator (e.g., an aerosol actuator or atomizer) in fluid connection with the cavity, for example, via a channel extending between a port of the actuator and the cavity, such that movement by the actuator exerts force on fluid from the cavity disposed in the channel, thereby causing the fluid to be ejected via the actuator port and through the pump and nozzle.

In an embodiment, the cavity is further fluidly connected to a valve, such as but not limited to a duckbill valve. Such a valve may be configured to allow fluid to flow therethrough, thereby filling the chamber with fluid. In this regard, each chamber may be refillable via such a valve. In another embodiment, the valve may be sealed (e.g., via a stopper) after fluid flows into the cavity such that the chamber is not refillable, for example, so that an end user of the chamber cannot refill or otherwise reuse the chamber for scent dispensing without needing to disassemble at least a portion of the chamber in order to add fluid to the cavity therein.

The nozzle, pump, and other components of the chamber may be assembled using a casing, and the cavity may be disposed in such a casing. The casing may include an opening through which at least a portion of the pump is movably disposed. The casing may further include a snap member which is configured to bend or otherwise distort when force is exerted thereon, and may lock into a respective hole in the tray once the chamber is fully inserted into the tray, thereby locking the chamber in place within the tray.

Each chamber may further have disposed therein or thereon a machine-readable tag or marker such as, but not limited to, a near field communication (NFC) tag, a QR code, a barcode, and the like. To this end, the casing of each chamber may further define a depression in which a tag is to be disposed such as, but not limited to, a depression defined in a bottom portion of the chamber. Such tags may be used for orientation by a scent dispensing device containing the tray and chambers. More specifically, an orientation of the drum relative to the chambers (e.g., an orientation defined with respect to positions of the chambers relative to an opening in a housing of the scent dispensing device through which scent is to be dispensed) may be determined by scanning or otherwise detecting the tags.

In an embodiment, the casing of each chamber may include a main portion in which the cavity and portions of certain other components are disposed, as well as a raised portion. The raised portion may extend from a top side of the main portion and may allow for convenient removal of the chamber from the tray by grasping sides of the raised portion (e.g., left and right sides) between a person's fingers, allowing for securing grip on the chamber which permits pulling the chamber out of the tray. To this end, in some further embodiments, at least some of the sides of the raised portion may be curved, for example, such that the contours of these sides substantially correspond in shape and size to a human's finger. Such a curved side design may improve a human's grip on the sides of the chamber, thereby allowing for more easily removing and inserting chambers into the tray.

In an embodiment, the drum has multiple compartments for insertion of respective chambers therein. Each compartment in the tray may be defined by a set of separating members as well as an enclosing member. Each compartment may further have defined one or more apertures therein. In a further embodiment, these apertures include a scanning aperture and a locking aperture. Each scanning aperture is defined in a location of the compartment such that when the portion of the drum containing that scanning aperture is aligned with a scanner, a tag to be scanned is exposed via the respective scanning aperture to the scanner. Each locking aperture is defined in a location of the compartment that corresponds to a snap member or other locking member that is adapted to lock the chamber in place within a respective compartment of the drum when such a locking member of the chamber is at least partially disposed in the locking aperture of that compartment.

In some embodiments, at least one of the compartments in the drum is defined as an orientation compartment, and a chamber inserted into such an orientation compartment may be designated as an orientation chamber.

In various embodiments, the modular scent dispenser is electronically controlled. More specifically, actuators in the scent dispenser may be caused to be moved via a system configured to provide input signals by converting such input signals into mechanical force, which in turn may be controlled via an electronic controller including a processing circuitry and a memory having instructions for controlling scent dispensing in accordance with various disclosed embodiments.

In such an embodiment, the electronic controller is configured to receive a command to dispense a scent, to determine an orientation of the chambers relative to one or more scent dispensing holes or other outlets through which scents are to be dispensed (e.g., a hole within a housing of the modular scent dispenser in which the chambers are disposed), to cause rotation of a tray containing the chambers in order to orient one or more of the chambers such that they align with respective to the apertures or outlets for dispensing scents, and to cause dispensing of one or more scents via one or more of the chambers (e.g., by causing movement of actuators in those chambers which results in fluid being expelled from a nozzle of each such chamber).

To facilitate such embodiments, the electronic controller may be further configured to control a motor, which in turn is configured to cause movement of one or more components in order to cause rotation of the drum. For example, the motor may cause rotation of a cog, thereby causing a series of cogs to turn until a cog that is in contact with a cog of the drum causes the drum to rotate. In this regard, the electronic controller may control rotation of the drum for purposes such as determining an orientation of the chambers in the drum, causing certain chambers to become aligned with the scent dispensing hole in order to enable dispensing of a scent of those chambers via the scent dispensing hole, and the like.

In an embodiment, each chamber is a cartridge including a cavity for storing scent essence and one or more components for ejecting the scent essence from the cavity. The chamber may further include a valve through which scent essence can be poured into the cavity from outside of the chamber. In a further embodiment, the components for ejecting the scent essence from each chamber include a pump and an actuator, where the pump is fluidly connected to the cavity such that scent essence fluid stored in the cavity can be pumped through a channel leading to the actuator. When fluid is pumped to the actuator, movement of the actuator (e.g., a downward depression caused by a pressing mechanism activated by a pressing motor) causes scent essence fluid to be sprayed or otherwise dispersed from the chamber.

Figure 1A:
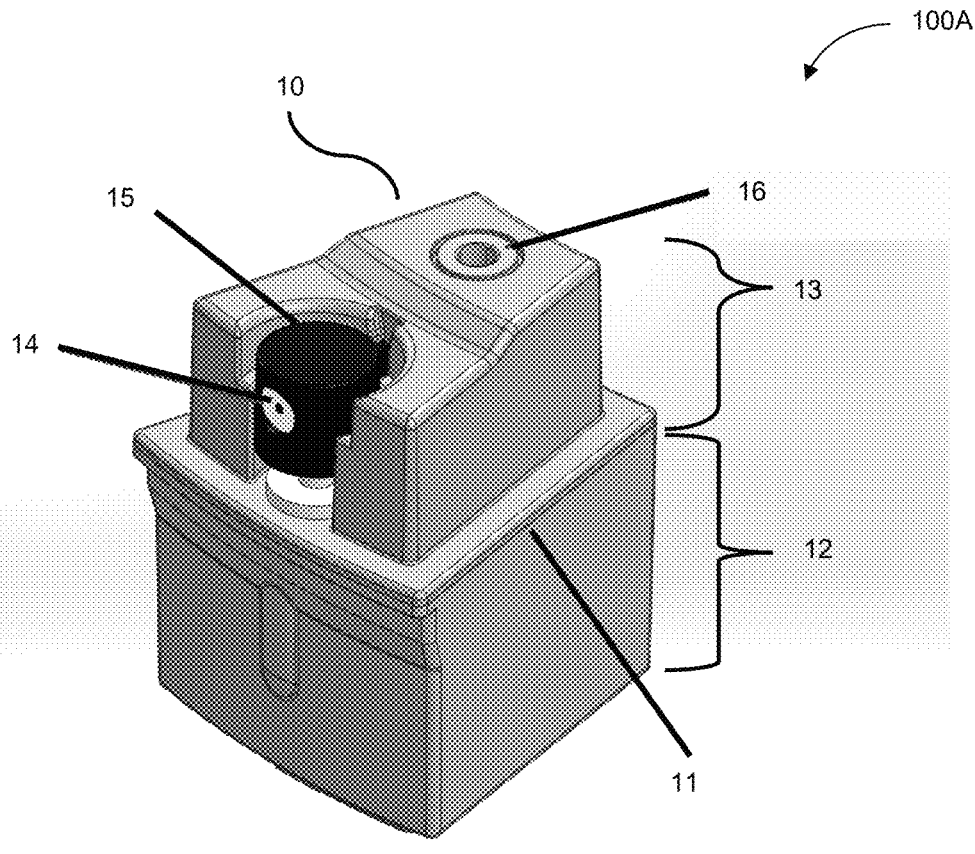
FIG. 1A is an illustration of a chamber of a modular scent dispenser according to an embodiment.

FIG. 1A is an illustration 100A of a chamber 10 of a modular scent dispenser according to an embodiment. As shown in FIG. 1, the chamber 10 includes a casing composed of a first bottom portion 12 and a second top portion 13. The top portion 13 further has components, including a nozzle 14, an actuator 15, and a valve 16. The bottom portion 12 and the top portion 13 may be affixed or otherwise attached such that they meet at an attachment line 11. To this end, the bottom portion 12 and the top portion 13 may be affixed via methods such as, but not limited to, welding (e.g., laser welded, ultrasonic welded, etc.), connecting via a locking mechanism (not shown), interlocking of components (not shown), and the like.

The nozzle 14 may be a spray nozzle or other nozzle configured to eject scent essence material such as, but not limited to, scent essence fluid. Accordingly, during operation, scent essence material stored within the chamber 10 (e.g., within a cavity such as the cavity 53 depicted in FIG. 5) may be pumped out of the chamber 10 via a pump (e.g., the pump 54 depicted in FIG. 5) and sprayed or otherwise ejected via the nozzle 14.

The spraying via the nozzle 14 may be facilitated by the actuator 15, that is, the actuator 15 is configured to produce force with respect to the nozzle 14 in order to displace at least a portion of the nozzle 14, thereby causing spraying via the nozzle 14 of scent essence material which has been pumped into the nozzle 14. To this end, the actuator 15 is configured to receive an input signal from a system (e.g., a system using a circuit board such as the PCB 89 discussed below) and to convert the input signal into mechanical energy in the form of force applied to the nozzle 14.

The valve 16 may be, but is not limited to, a duckbill valve or other valve which allows fluid to pass therethrough in at least one configuration. As discussed herein, a cavity (not shown in FIG. 1A) of the chamber 10 may be filled with scent essence fluid or other scent essence material by pouring or otherwise depositing such material into the valve 16 and then letting such material pass through the valve 16 into such a cavity.

Figure 1B:
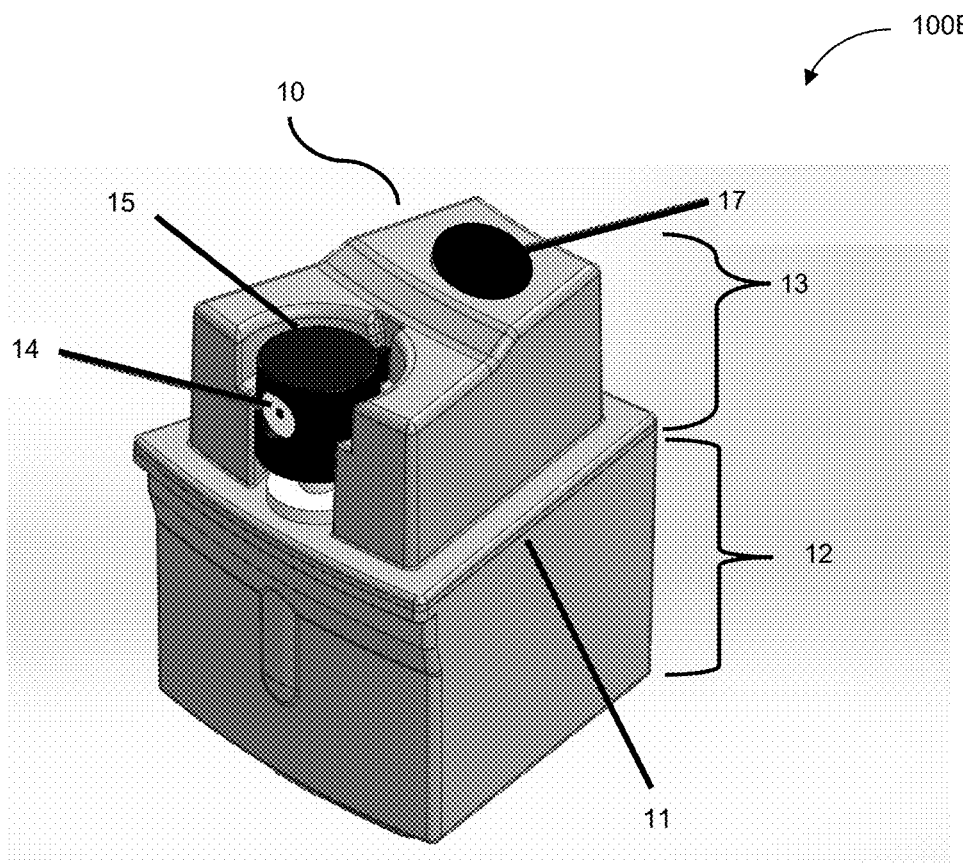
FIG. 1B is an illustration of a chamber according to another embodiment.

FIG. 1B is an illustration 100B of the chamber 10 according to another embodiment. More specifically, in the embodiment shown in FIG. 1B, the chamber 10 includes a stopper 17 disposed so as to seal the chamber 10 such that fluid or other materials cannot enter or exit the chamber 10. Such a stopper 17 may be used to prevent fluid from exiting or entering the chamber 10. In some embodiments, the stopper 17 may be glued or otherwise affixed to the chamber 10 after the chamber 10 has been filled, thereby preventing the chamber 10 from being refilled without damaging the chamber or otherwise removing the adhesive or other fixture affixing the stopper 17 to the chamber 10. The stopper 17 may be used instead of the valve 16 or may be used to seal the valve 16.

In such an embodiment, the chamber 10 may be disposable rather than reusable, and the chamber 10 may be sold as units which come pre-filled with scent essence fluid such that a scent dispensing device including the chambers can be effectively refilled by purchasing new chambers and placing the new chambers within a drum of the scent dispensing device.

Figure 2A:
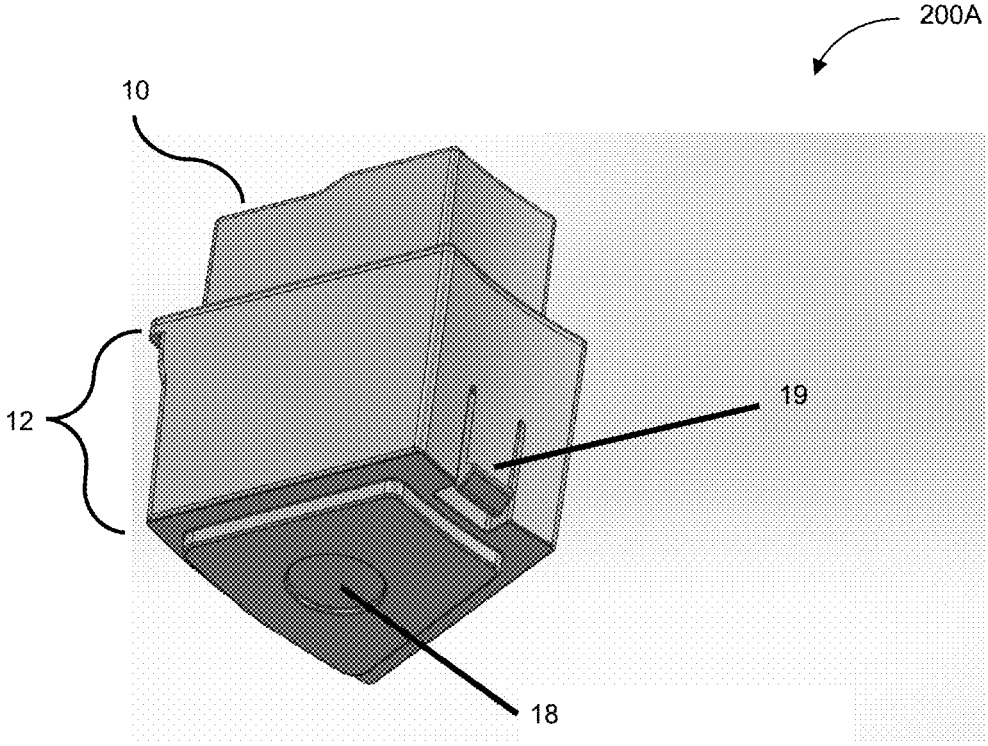
FIG. 2A is an illustration showing another view of the chamber according to an embodiment.

FIG. 2A is an illustration 200A showing another view of the chamber 10 according to an embodiment. More specifically, the other view of the chamber illustrates a depression 18 in as well as a snap member 19 in the bottom portion 12.

The depression 18 may be designed to receive a tag or other machine-readable marker, for example, a near-field communication (NFC) tag. As discussed below, such a tag may be utilized to transmit or otherwise convey information about the chamber 10 such as, but not limited to, a predetermined type of scent essence of the chamber 10 or an identifier of the chamber 10. The machine-readable marker may further be writeable, i.e., is capable of being written to such that data written to the machine-readable marker while the machine-readable marker is disposed in a scent dispensing device may be subsequently read.

The snap member 19 is adapted to allow for locking an intersection of the chamber 10 into a drum such as, but not limited to, the drum 30, FIG. 3. More specifically, the snap member 19 may be adapted to bend or otherwise at least partially deform in response to force exerted while inserting the chamber 10 into the drum and to return to a default position (i.e., pre-defamation position) once the chamber 10 is locked into place. Accordingly, the snap member 19 aids in modularly inserting the chamber 10 such that the chamber 10 can be readily removed and replaced as desired.

Figure 2B:
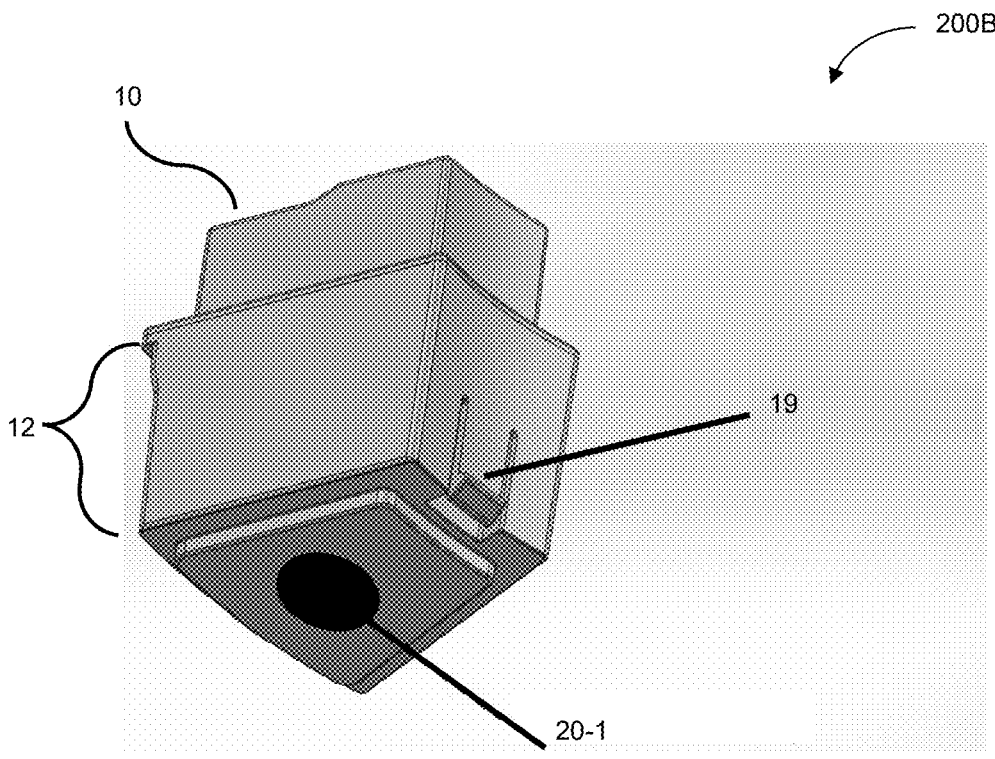
FIG. 2B is an illustration showing another view of the chamber having a machine-readable tag inserted therein according to an embodiment.

FIG. 2B is an illustration 200B showing another view of the chamber having a tag inserted therein according to an embodiment. As shown in FIG. 2B, the bottom portion 12 of the chamber 10 has a tag 20-1 inserted into the depression 18 of FIG. 2A. The tag 20-1 may be, but is not limited to, a NFC tag configured to transmit data which may be utilized to detect a presence of the chamber 10 at a particular position within a scent dispensing device as described herein.

It should be noted that the tag 20-1 is depicted as being round merely for example purposes, and that the disclosed embodiments are not limited as such. Other shapes such as, but not limited to, square or otherwise rectangular shapes, may be used as the shape for the tag 20-1 without departing from the scope of the disclosure. In any such variations, the depression 18 may be shaped and sized such that the tag 20-1 fits tightly in the depression 18. In other words, in such embodiments, the depression 18 may substantially conform in shape and size to the tag 20-1 such that the tag is secured in place once the tag 20-1 is inserted into the depression 18.

Figure 2C:
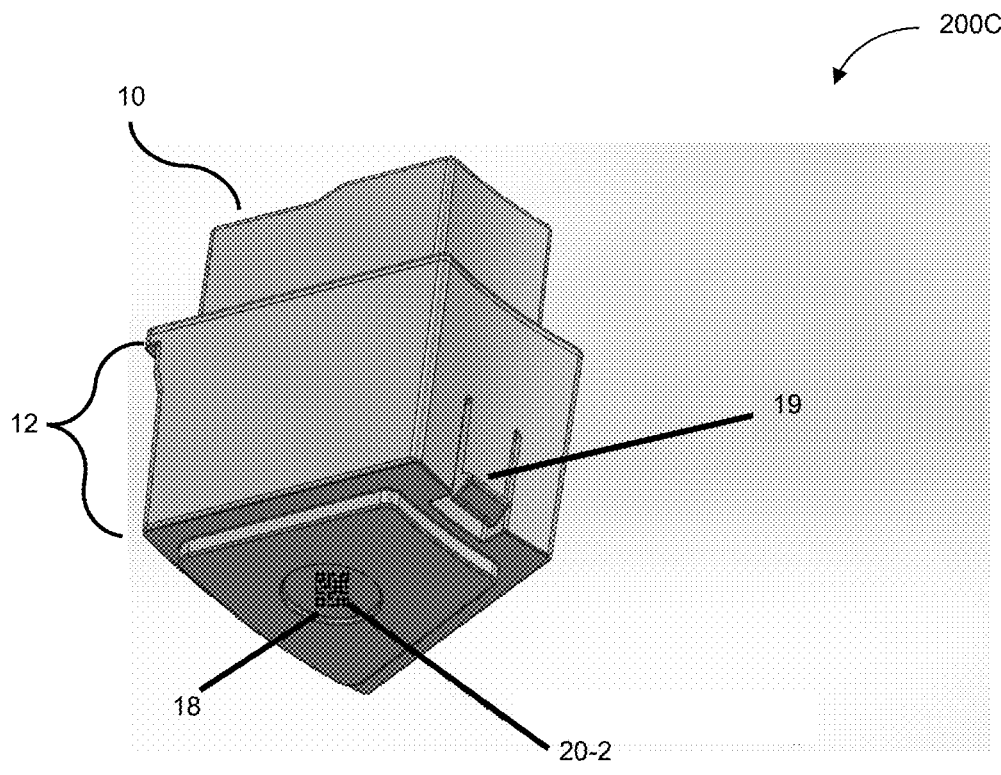
FIG. 2C is an illustration showing an alternative embodiment of the chamber having a machine-readable marker printed in a depression.

FIG. 2C is an illustration 200C showing an alternative embodiment of the chamber 10 having a machine-readable marker 20 printed in the depression 18. In the example implementation shown in FIG. 2C, the machine-readable marker 20 is realized as a quick response (QR) code 20-2. In other implementations (not shown), other types of markings which may be read by a computer or other machine may be utilized such as, but not limited to, a barcode. The machine-readable marker 20 contains data related to the chamber 10 such as, but not limited to, a type of scent essence fluid disposed in the chamber 10, an identifier of the chamber 10, and the like. Consequently, when the machine-readable marker 20 is read by a scanner of a system performing scent dispensing as described herein (e.g., as discussed further below with respect to FIG. 12), the system is configured to determine a type of scent essence disposed in the chamber (either directly based on data explicitly indicating the type of scent essence obtained via the reading or indirectly based on data indicating the identifier of the chamber 10 obtained via the reading combined with other data indicating a type of scent essence disposed in a chamber having that identifier).

Figure 2D:
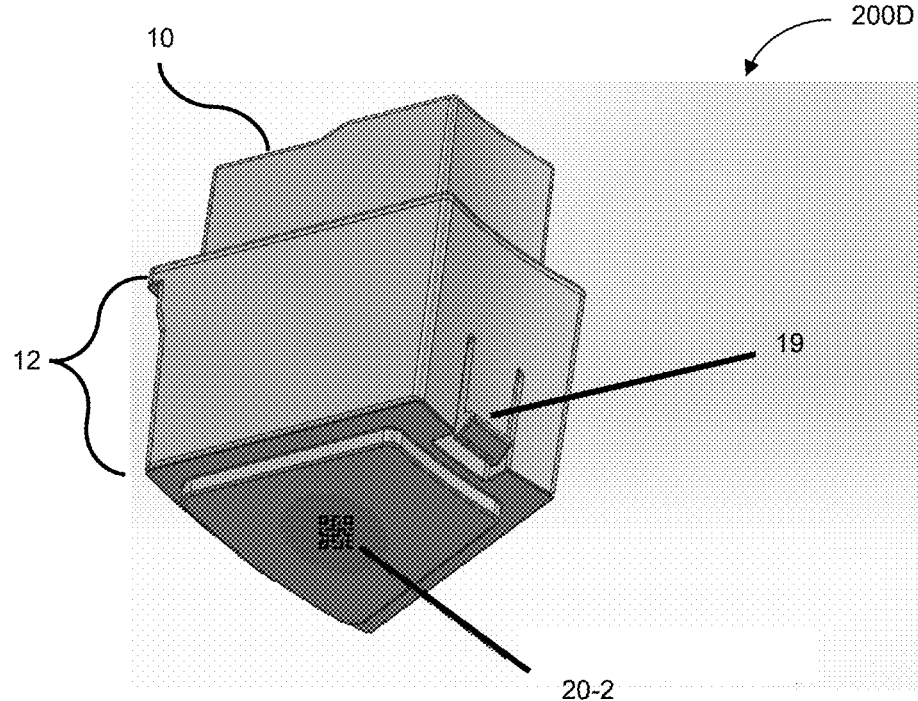
FIG. 2D is an illustration featuring a machine-readable marker printed on a flat surface of a bottom portion of a chamber.

It should be noted that the depression 18 may be utilized for convenient insertion of the tag 20-1 or may be utilized as a location for the machine-readable marker 20, but that the machine-readable marker 20 may be stamped or otherwise printed on the bottom portion 12 of the chamber 10 without any depression. Accordingly, in at least some embodiments, the chamber 10 may exclude the depression 18. An example of such an embodiment is shown in FIG. 2D, which shows an example illustration 200D featuring the machine-readable marker in the form of a QR code 20-2 printed on a flat (non-depression) surface of the bottom portion 12 of the chamber 10.

Figure 3A:
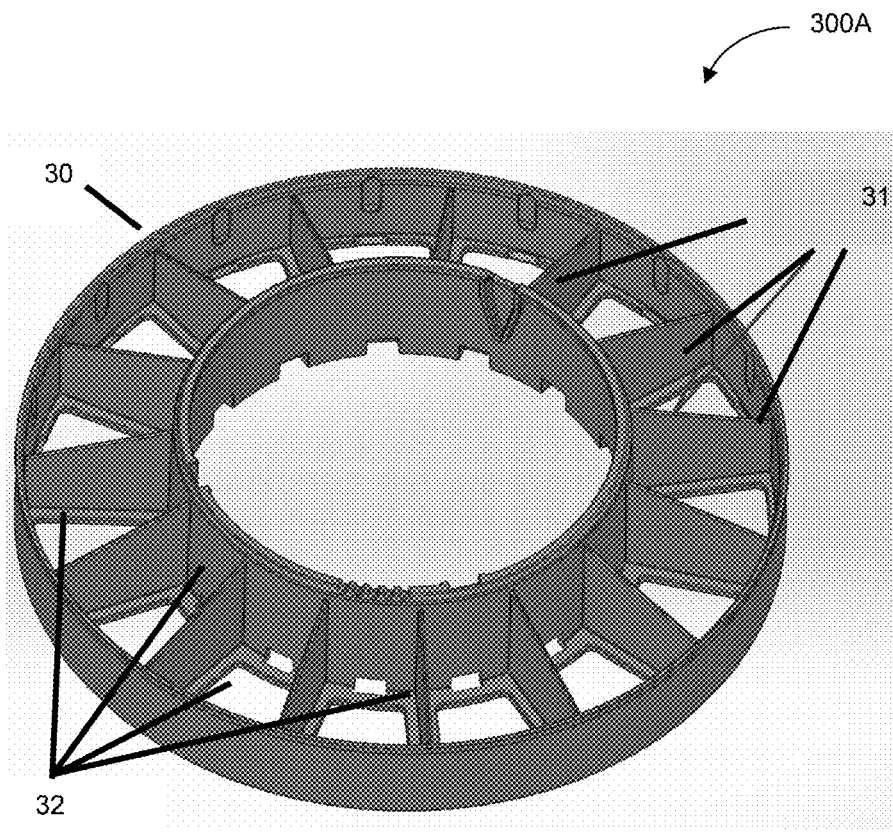
FIG. 3A is an illustration showing a drum of a modular scent dispenser according to an embodiment.

FIG. 3A is an illustration 300A showing a drum 30 of a modular scent dispenser according to an embodiment. As shown in FIG. 3, the drum 30 has multiple separating members 31 which section the drum 30 into multiple compartments 32. Specifically, in the embodiment depicted in FIG. 3, each compartment 32 is formed by a respective pair of the separating members 31 along with bottom and central walls of the drum 30. Each compartment 32 is sized and shaped in order to accommodate receiving a respective chamber (e.g., chambers such as the chamber 10, FIG. 1, or the chamber 60, FIG. 6).

Figure 3B:
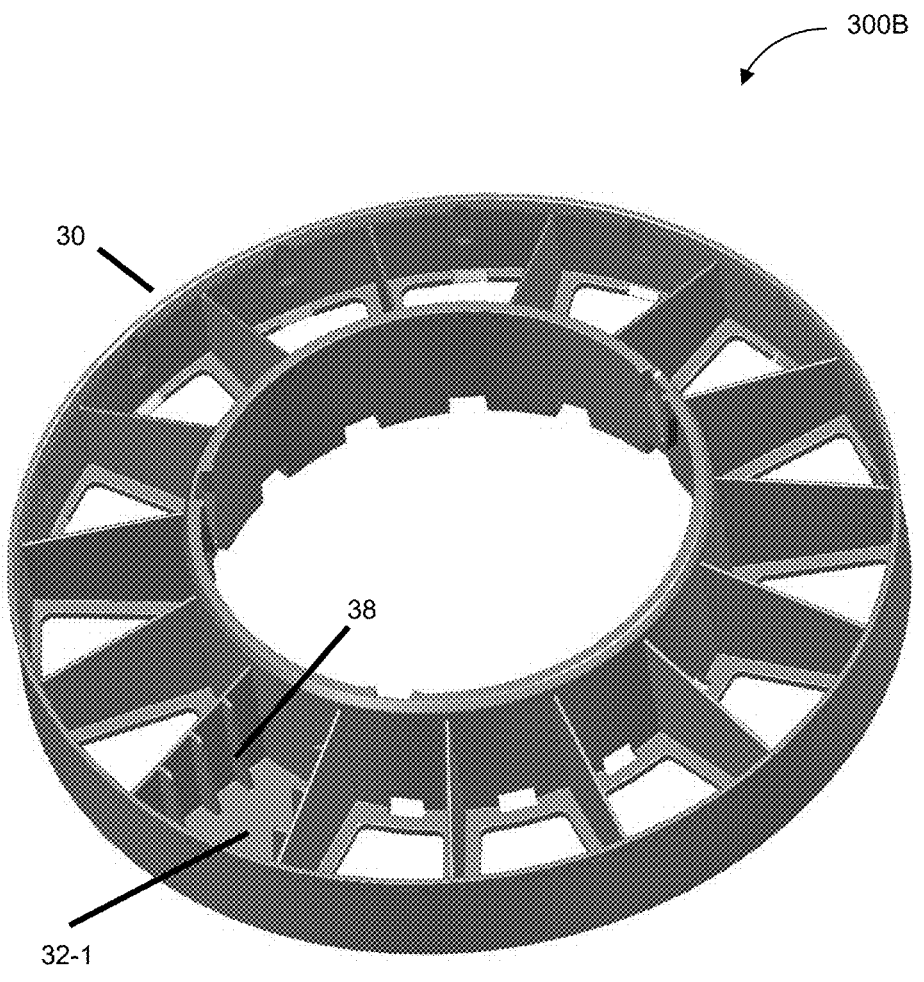
FIG. 3B is an illustration showing a drum of a modular scent dispenser having a closed compartment according to another embodiment.

FIG. 3B is an illustration 300B showing the drum 30 in which a first compartment 32-1 is closed, i.e., lacks apertures such as the apertures 33 and 34 discussed further below with respect to FIG. 4A.

Figure 3C:
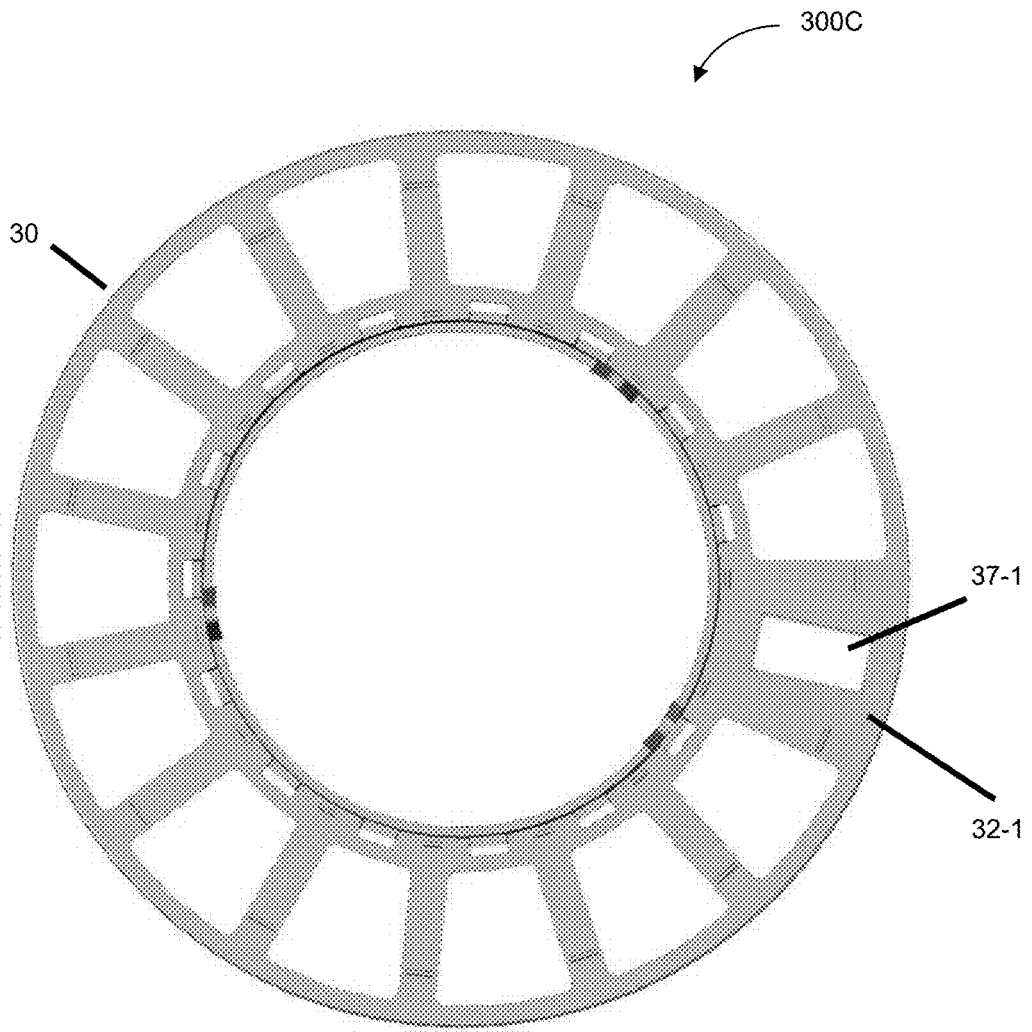
FIG. 3C is an illustration showing a bottom view of the drum of the modular scent dispenser having a closed compartment according to the other embodiment.

FIG. 3C is an illustration 300C showing a bottom view of the drum 30 having the first closed compartment 32-1. As shown in FIG. 3C, the closed compartment 32-1 has a tag 37-1 disposed on the bottom of the closed compartment 32-1. Such a tag 37-1 may be configured to provide data indicating a type of the drum, for example, whether the drum is a modular drum or a non-modular drum, which in turn may be utilized to determine which scent dispensing protocols to apply as discussed further below with respect to FIG. 12.

Figure 3D:
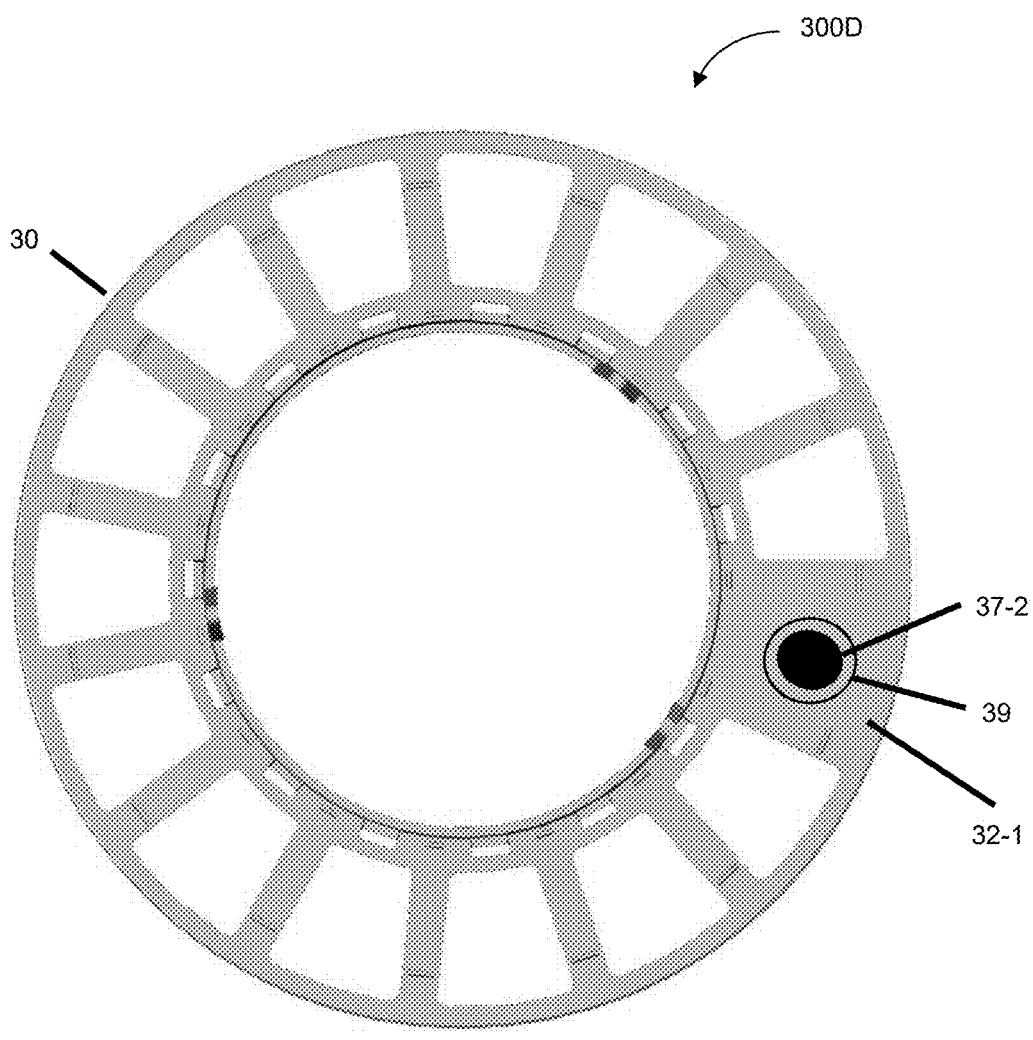
FIG. 3D is an illustration showing a bottom view of the drum of the modular scent dispenser having a closed compartment according to another embodiment.

FIG. 3D is an illustration 300D showing a bottom view of the drum 30 having the first closed compartment 32-1 according to another embodiment. As shown in FIG. 3D, the closed compartment 32-1 has a tag 37-2 disposed on the bottom of the closed compartment 32-1. The tag 37-2 may be configured to provide data indicating a type of the drum, for example, whether the drum is a modular drum or a non-modular drum, which in turn may be utilized to determine which scent dispensing protocols to apply as discussed further below with respect to FIG. 12.

In the embodiment depicted in FIG. 3D, a tag 37-2 is disposed in a depression 39 of the drum 30. It should be noted that the tag 37-2 is depicted as being round merely for example purposes, and that the disclosed embodiments are not limited as such. Other shapes such as, but not limited to, square or otherwise rectangular shapes, may be used as the shape for the tag 37-2 without departing from the scope of the disclosure.

It should also be noted that the depression 39 is depicted as being visibly larger than the tag 37-2 merely for illustrative purposes in order to show the location of the tag 37-2 relative to the depression 39 (i.e., disposed in the depression), but that the depression 39 is not limited to the size relative to the tag 37-2 depicted in FIG. 3D. In any such variations, the depression 39 may be shaped and sized such that the tag 37-2 fits tightly in the depression 39. In other words, in such embodiments, the depression 39 may substantially conform in shape and size to the tag 37-2 such that the tag 37-2 is secured in place once the tag 37-2 is inserted into the depression 39.

Figure 4A:
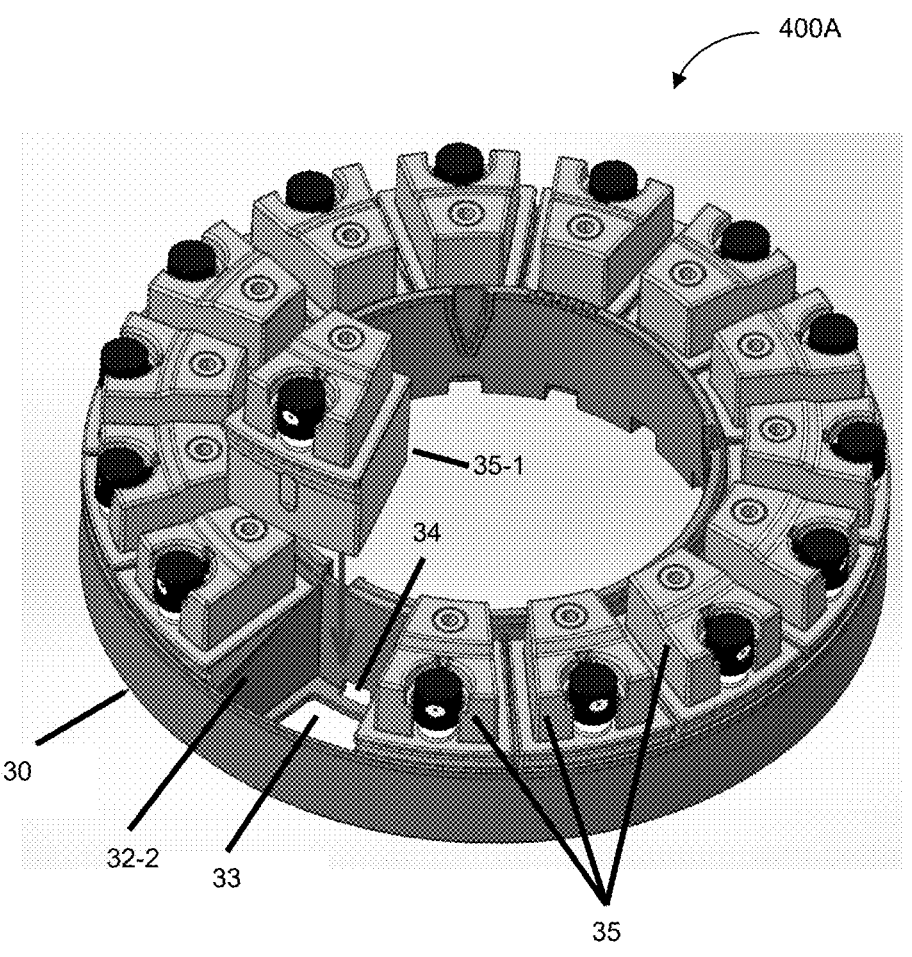
FIG. 4A is an illustration showing a drum with a compartment open according to an embodiment.

FIG. 4A is an illustration 400A showing the drum 30 with an open compartment 32-2 exposed according to an embodiment. In the illustration 400A, the drum 30 has multiple chambers 35 inserted therein, and the chamber 35-1 is displaced in order to illustrate the open compartment 32-2.

The open compartment 32-2 illustrated in FIG. 4A is open at least insofar as it includes a first scanning aperture 33 and a second locking aperture 34. The scanning aperture 33 may be utilized to expose a machine-readable marker (e.g., the tag 20-1 or the QR code 20-2) of the chamber 10 to a scanner (not shown in FIG. 4A) in order to enable scanning the machine-readable marker via the scanner for purposes such as determining a type of scent essence fluid disposed in the chamber 10. In particular, the scanning aperture 33 may expose a barcode or QR code such that a light-based scanner can read the barcode or QR code. It should be noted that the scanning aperture 33 may be excluded in some embodiments, for example, when the machine-readable marker is a tag which may be scanned through a solid bottom such as, but not limited to, a NFC tag.

Figure 4B:
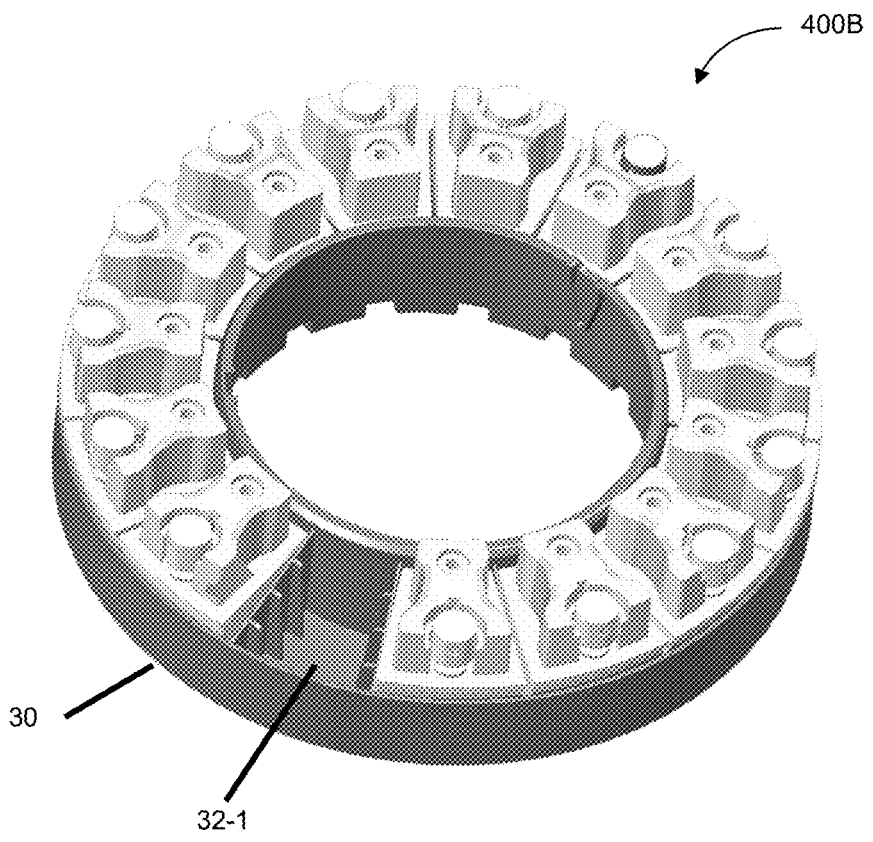
FIG. 4B is an illustration showing a drum with a closed compartment exposed according to an embodiment.

FIG. 4B is an illustration 400B showing the drum 30 with a closed compartment 32-1 exposed according to an embodiment. The closed compartment 32-1 lacks the scanning aperture 33 of the open compartment 32-2. In some embodiments, the closed compartment 32-1 acts as a dummy compartment. In such embodiments, the closed compartment 32-1 may further have a tag (e.g., the tag 37, not shown in FIG. 4B) configured to provide data indicating a type of the drum 30 (e.g., modular or non-modular).

In some embodiments, the closed compartment 32-1 may further have one or more ribs 38 along the side walls of the closed compartment 32-1 Such ribs 38 may be utilized in order to prevent insertion of a chamber into the closed compartment 32-1.

Figure 5:
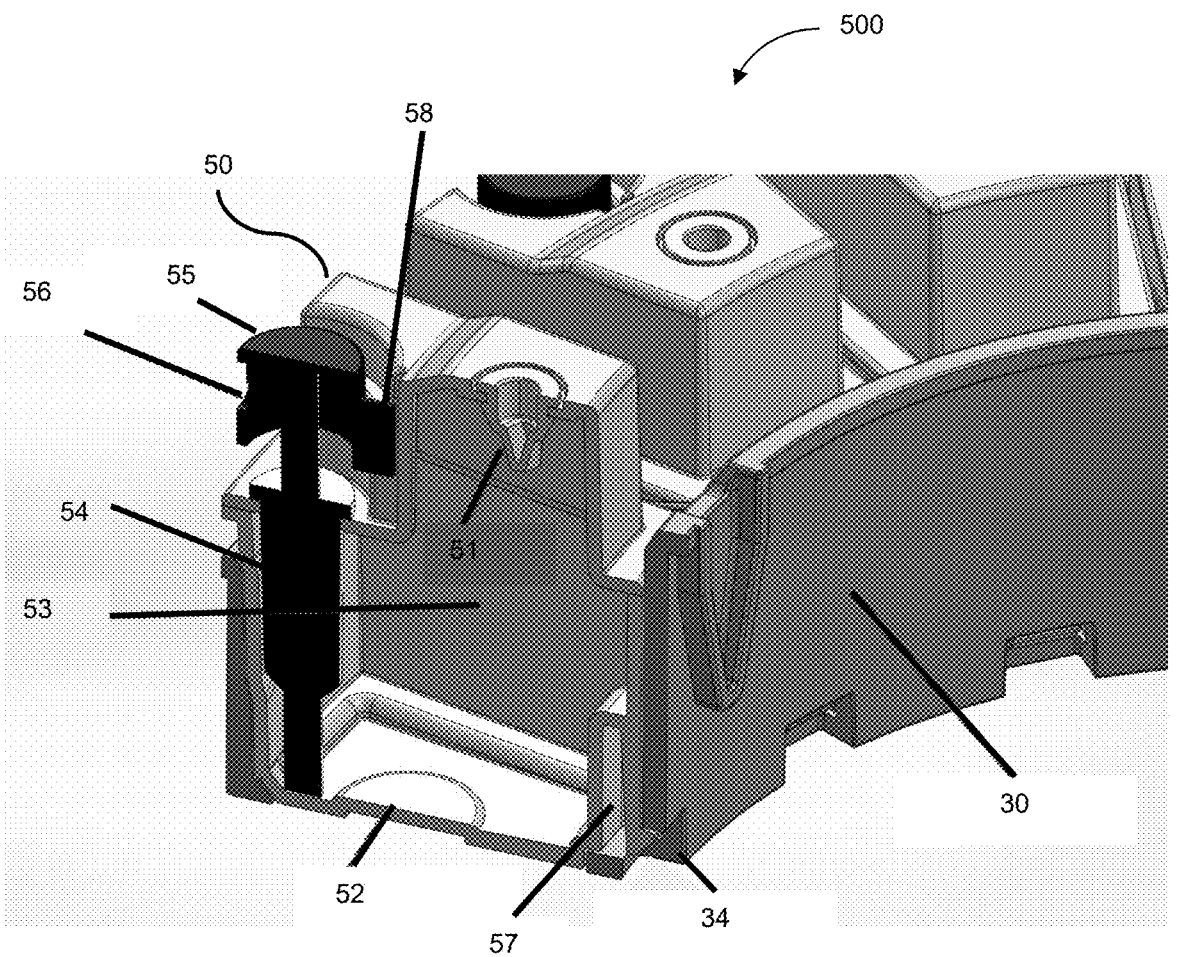
FIG. 5 is a cross-sectional view of a portion of an assembled modular scent dispenser according to an embodiment.

FIG. 5 is a cross-sectional view 500 of a portion of an assembled modular scent dispenser according to an embodiment. More specifically, the cross-sectional view 500 illustrates a cross-section of a chamber 50 disposed in the drum 30. The cross-section of the chamber 50 demonstrates cross-sections of various components of the chamber 50 including a valve 51, a depression 52, a cavity 53, a pump 54, an actuator 55, a nozzle 56, and a snap 57.

As noted above, the valve 51 may be, but is not limited to, a duckbill valve. The valve 51 may be utilized in order to fill the chamber 50 with scent essence (e.g., a scent essence fluid, not shown). More specifically, fluid or other material may be poured or otherwise provided to the valve 51 and may pass through the valve 51 into the cavity 53, thereby at least partially filling the cavity 53. It should be noted that a valve 51 is depicted for example purposes, but that the disclosed embodiments are not necessarily limited as such. In some implementations, the valve may be replaced with a hole which is sealed after scent essence fluid is poured via that hole into the chamber 50.

When the cavity 53 has scent essence fluid or other material disposed therein, such material may be ejected from the chamber 50 via the pump 54 and the actuator 55. To this end, the pump 54 may be configured to pump fluid from the cavity 53 upward through the pump 54 such that the fluid exits via a nozzle 56. Moreover, the actuator 55 may cause displacement of the nozzle 56 in order to cause fluid in the nozzle 56 to be sprayed therefrom. Such action by the pump 54 and the actuator 55 may be powered by a motor (not shown in FIG. 5).

To this end, in an embodiment, the pump 54 is in fluid connection with both the cavity 53 and the nozzle 56. A channel in the pump 54 may allow fluid to pass through, thereby allowing fluid to be pumped from the cavity 53 to the nozzle 56. To this end, the pump may be spring-loaded or otherwise configured to pump fluid.

The snap 57 may be used to lock the chamber 50 in place within the drum 30. To this end, as shown in FIG. 5, the snap 57 is placed such that it is at least partially disposed in a locking aperture 34. While being placed into the drum 30, the snap 57 may deform until the snap 57 is lowered such that part of the snap locks into place within the locking aperture 34.

As shown in FIG. 5, the actuator 55 has a fin 58. The fin 58 may be used to prevent the actuator 55 from rotating, for example as discussed further below with respect to FIGS. 14, 17, 19, and 20.

It should be noted that, in some embodiments, the valve 51 may be sealed after fluid is poured into the cavity 53, or a sealing stopper (such as the stopper 17, not shown in FIG. 5) may be placed instead of the valve 51 in order to seal the chamber 50 and prevent fluid from going in or coming out of the chamber except via the pump 54, actuator 55, and nozzle 56.

Figure 6:
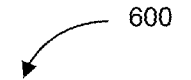
FIG. 6 is a top view of a chamber having a curved wall according to an embodiment.
Figure 6:
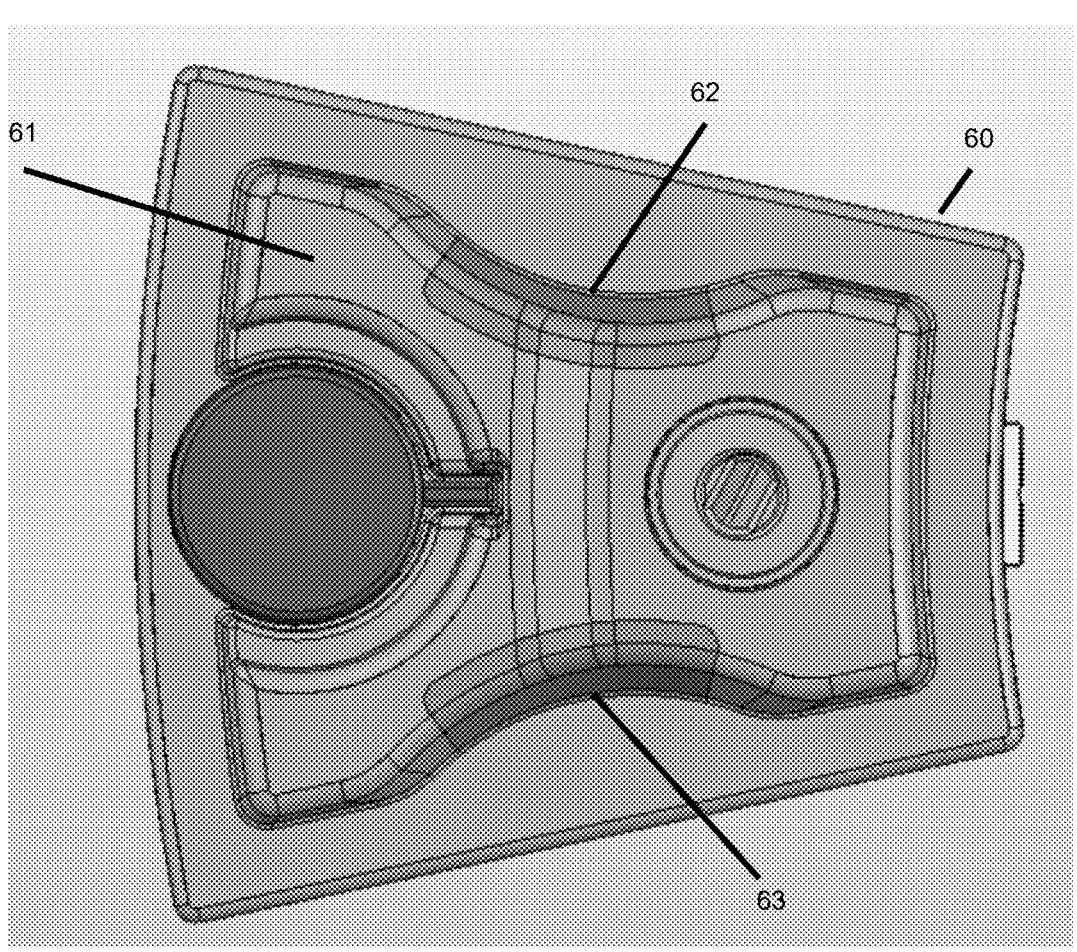

FIG. 6 is a top view 600 of a chamber 60 having a curved wall according to an embodiment. The curved wall design of the chamber 60 may be utilized to improve grip on the chamber 60, for example, when the chamber 60 is inserted into or removed from a drum such as the drum 30.

As depicted in FIG. 6, the chamber 60 has an upper portion 61 featuring a first curved wall 62 and a second curved wall 63. The curved walls 62 and 63 may be shaped and sized to substantially correspond to a shape and size of an average human adult's fingers such as, but not limited to, the thumb and index fingers, such that a human may grasp the chamber 60 by the curved walls 62 and 63. This design therefore facilitates the modular nature of the chamber 60 by aiding a human in moving the chamber relative to the drum in which it was or will be disposed.

In an embodiment, the curved walls 62 and 63 have smooth surfaces. In another embodiment, the curved walls 62 and 63 have rough, uneven, or otherwise non-smooth surfaces. Such non-smooth surfaces may further improve grip when a person picks up the chamber 60 by the curved walls 62 and 63.

Figure 7:
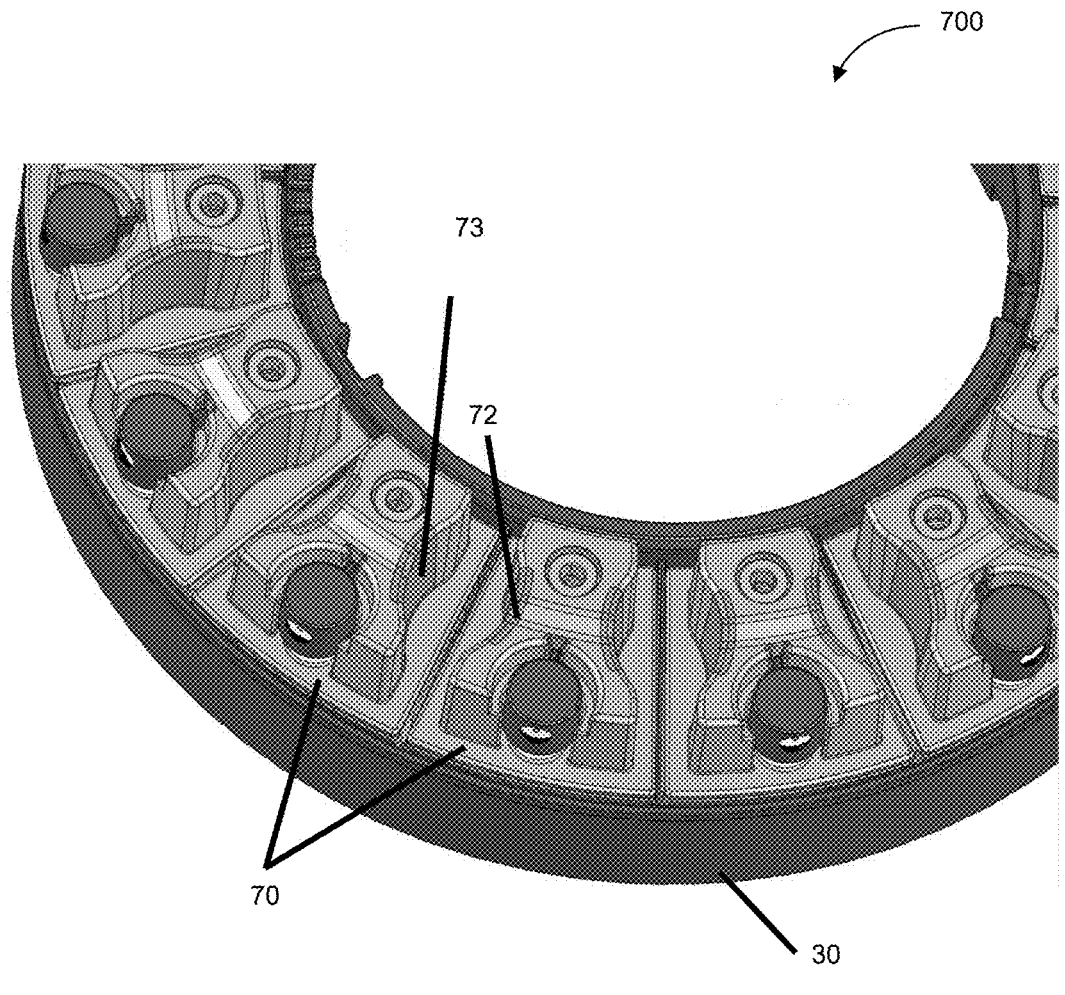
FIG. 7 is an illustration showing chambers having curved walls inserted into a drum according to an embodiment.

FIG. 7 is an illustration 700 showing chambers 70 having curved walls 72 and 73 inserted into the drum 30 according to an embodiment. Each of the chambers 70 may be designed as discussed above with respect to FIG. 6, and has a respective pair of first and second curved walls 72 and 73.

Figure 8:
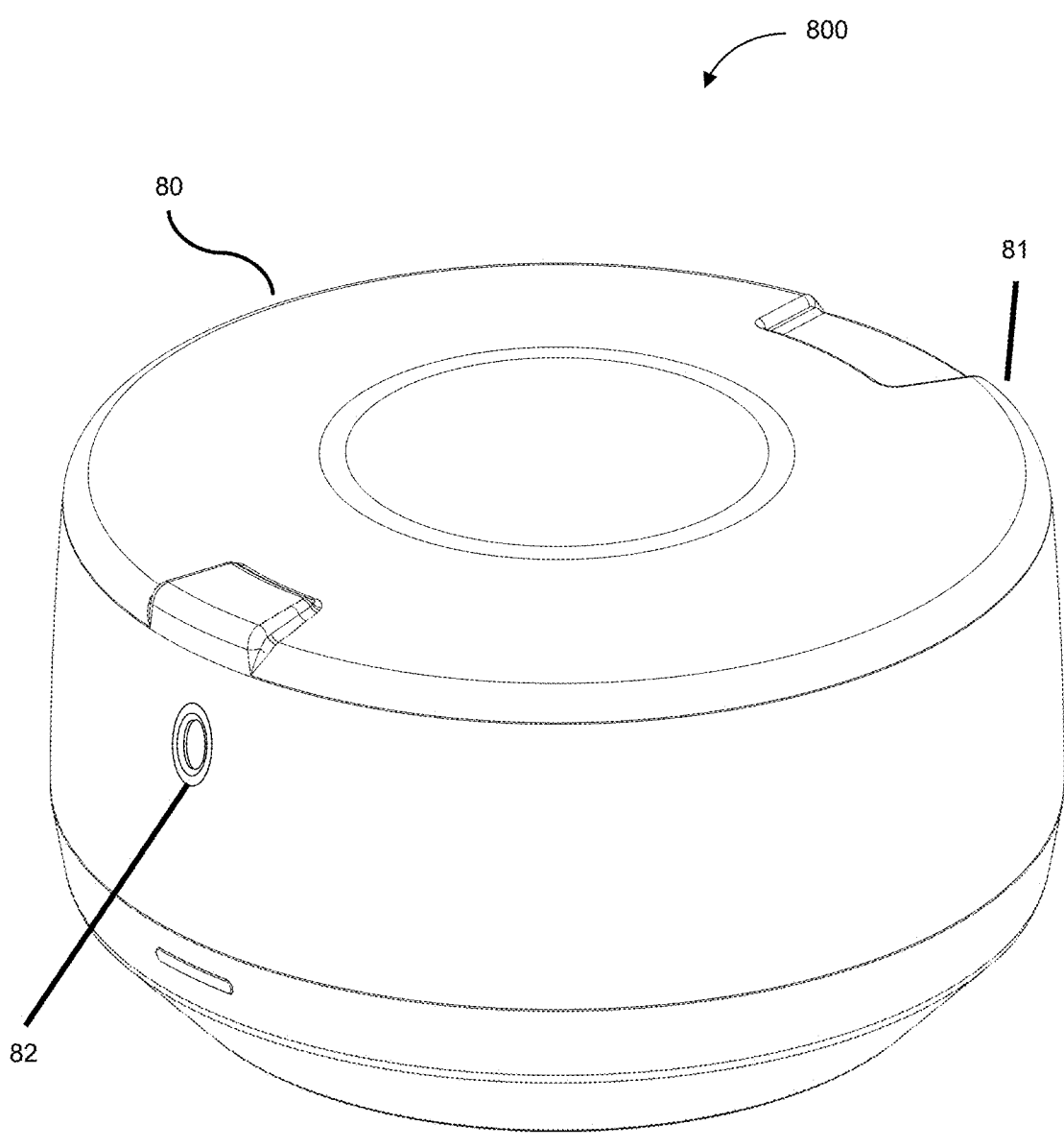
FIG. 8 is a perspective view of a housing of a modular scent dispenser in accordance with various disclosed embodiments.

FIG. 8 is a perspective view 800 of a housing 81 of a modular scent dispenser 80 in accordance with various disclosed embodiments. The modular scent dispenser 80 may act as a scent dispensing device and may be modular via use of a drum with modular chambers such as the drum 30 and chamber 10 or curved upper wall chamber 60 discussed above.

In the embodiment shown in FIG. 8, the housing 81 includes a scent dispensing hole 82. The scent dispensing hole 82 may be utilized such that scents are dispensed by aligning a chamber with the scent dispensing hole 82 and causing a component of the chamber (e.g., an actuator) to eject scent essence fluid therefrom, where the scent essence fluid moves through the scent dispensing hole 82, thereby dispensing the scent in a surrounding environment (not shown). More specifically, scent essence fluid may be ejected from a spray nozzle (e.g., the nozzle 14).

Figure 9:
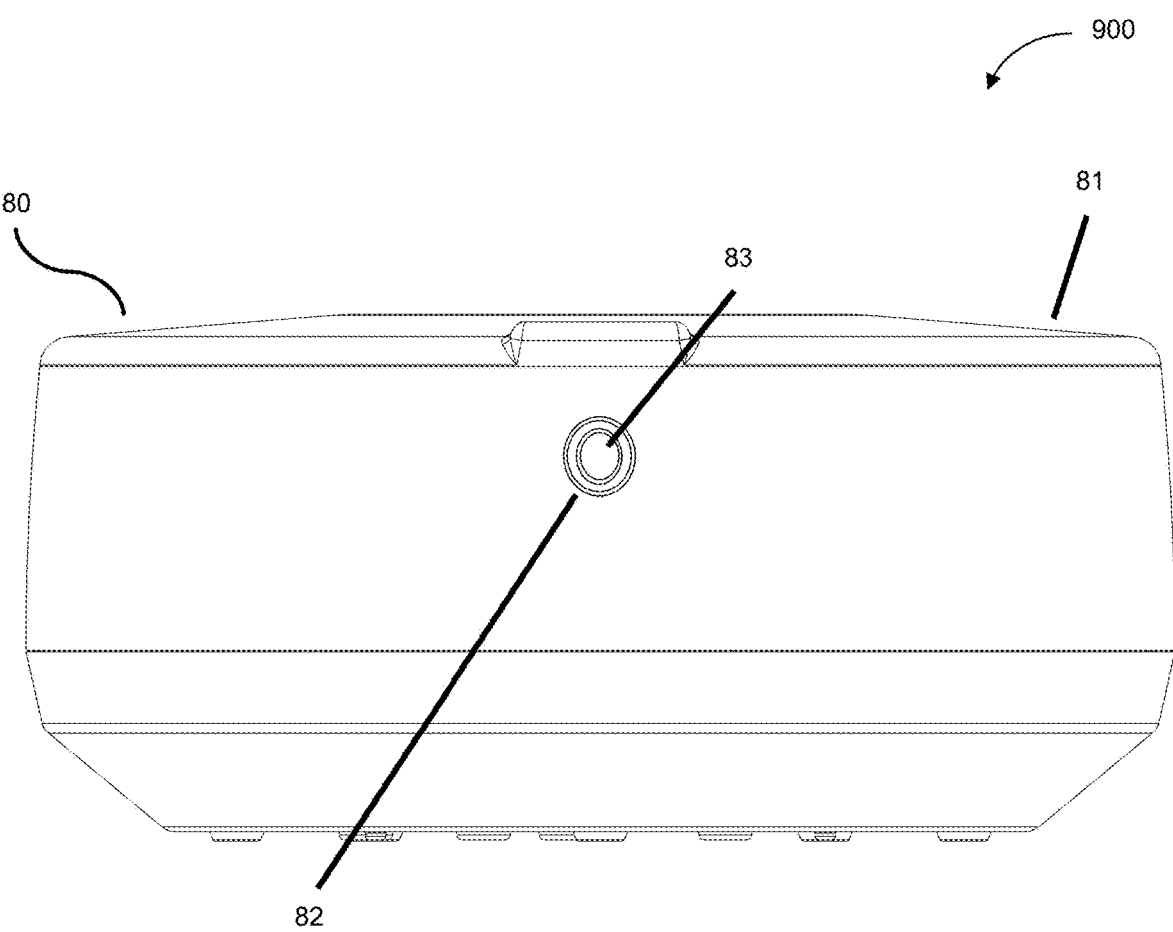
FIG. 9 is a front view of a housing of a modular scent dispenser utilized to illustrate a nozzle of a chamber disposed in the modular scent dispenser being deployed for scent dispensing in accordance with various disclosed embodiments.

FIG. 9 is a front view 900 of the housing 81 of the modular scent dispenser utilized to illustrate a nozzle of a chamber disposed in the modular scent dispenser 80 being deployed for scent dispensing in accordance with various disclosed embodiments. As depicted in FIG. 9, the scent dispensing hole 82 in the housing 81 has been aligned with a nozzle 83 of a chamber (e.g., a spray nozzle such as the nozzle 14). Consequently, when scent essence fluid is sprayed out of the nozzle 83, the scent essence fluid passes through the scent dispensing hole 82 and is dispensed into the surrounding environment.

FIG. 10 is an illustration 1000 of a bottom portion 84 of a scent dispenser assembly demonstrating components utilized for causing movement of the actuators which may be utilized in accordance with various disclosed embodiments. More specifically, FIG. 10 illustrates a motor 85 which may be mechanically connected to one or more cogs (e.g., the cog 88-1, FIG. 11) in order to enable rotation of the drum. In other words, the motor 85 may cause rotation of a series of cogs, which in turn may be mechanically connected to the drum, thereby causing the drum to rotate. Such rotation may be utilized for determining chamber statuses and causing dispensing of scents as described herein.

To this end, the bottom portion 84 further includes a platform 86 which may be rotated via the motor 85 and one or more cogs. During operation, a drum (e.g., the drum 30) may be disposed on the platform 86 such that, when the platform 86 rotates due to the motor 85, the drum also rotates. This rotation of the drum may be performed in order to change which chamber in the drum is aligned with a scent dispensing hole in the housing 81.

In an embodiment, the bottom portion 84 further includes a shaft 87. The shaft 87 may be connected to another motor (e.g., a pressing motor, FIG. 21) which causes at least a portion of the shaft 87 to move upward as part of a mechanism (e.g., the mechanism 2100, FIG. 21) configured to cause actuators to move in order to dispense fluid. A non-limiting example of such a mechanism is described further below with respect to FIG. 21.

In an embodiment, the scent dispenser assembly further includes a scanner 101. The scanner 101 is configured to scan machine-readable markers as described herein. In a further embodiment, the scanner 101 is configured to scan machine-readable markers of chambers, of a drum, or both.

FIG. 11A is a bottom interior view 1100A which may be utilized in accordance with various disclosed embodiments. The bottom portion 84 includes the PCB 89, and the PCB 89 may be utilized to realize scent dispensing as described herein. To this end, the PCB 89 may include a processing circuitry and a memory (not shown in FIG. 11), where the memory contains instructions which, when executed by the processing circuitry, configure the PCB 89 to control the motor 85 or another motor (e.g., a pressing motor configured to cause one or more components to press on actuators such as the rotating motor 211, FIG. 21) in order to cause such motors to power one or more other components of the scent dispensing device. To this end, the PCB 89 is electrically connected to such motors in order to enable causing the motor 85, the other motor, or both, to move.

The bottom interior view 1100A further illustrates a set of cogs 88-1 and 88-2 which may be mechanically connected to the motor 85 in order to enable rotation of a drum (for example, by causing rotation of the platform 86 upon which a drum such as the drum 30 is disposed). More specifically, the cog 88-1 may be mechanically connected to the motor 85 such that the motor 85 may cause the cog 88-1 to turn, which consequently causes the cog 88-2 to turn. The cog 88-2 may be included in or further mechanically connected to the platform 86 such that the platform 86 turns as the cog 88-2 turns. In other words, such a mechanical connection involves the motor 85 being connected to one or more other components which ultimately cause mechanical rotation of the cog 88-1.

FIG. 11B is a bottom interior view 1100B showing placement of a printed circuit board (PCB) 89 on the bottom portion 84 which may be utilized in accordance with various disclosed embodiments. The PCB 89 may include a processing circuitry and memory. The memory may store instructions for performing at least a portion of the disclosed embodiments such as, but not limited to, the method described with respect to FIG. 12.

FIG. 12 is a flowchart 1200 illustrating a method for dispensing scent using orientation detection with respect to a modular scent dispenser according to an embodiment. In an embodiment, the method is performed by a scent dispenser having at least a processing circuitry and a memory, where the method is performed by executing instructions stored in the memory via the processing circuitry. An example hardware layer which may be utilized to realize the method of FIG. 12 is discussed further below with respect to FIG. 13.

At optional S1210, a type of drum is determined. Specifically, the type of drum may be determined as a type of a drum including chambers in a scent dispensing device which is to be used for dispensing scents such as one of the drums of the scent dispensing devices described herein.

In an embodiment, S1210 includes scanning a tag of a closed compartment (e.g., the tag 37 of the closed compartment 32-1, FIG. 3B). Such a tag may, when scanned, provide data indicating a type of the drum. Non-limiting example types of drums include modular and non-modular drums. In a further embodiment, the steps following S1210 may be performed differently depending on a type of the drum. To this end, in yet a further embodiment, S1210 may include determining a protocol to be used for subsequent execution based on the determined type of drum.

At S1220, one or more machine-readable markers are scanned. In an embodiment, the machine-readable markers correspond to respective chambers of a scent dispensing device such that each marker effectively represents its respective chamber. The machine-readable markers may be or may include, but are not limited to, barcodes, computer-readable chips (e.g., NFC tags), and the like.

In an embodiment, S1220 includes building a map of the drum of the scent dispensing device. Such a map may include positions of the chambers within the drum relative to a starting position such as, but not limited to, a starting position realized as a position of a closed compartment such as the closed compartment 32-1, FIG. 3B. In this regard, the position of the drum needed for dispensing respective scents may be determined using the positions of the chambers relative to positions in the drum, for example, a position defined with respect to a number of rotational iterations in which the drum, at each iteration, is rotated such that the next chamber in the drum becomes aligned with an outer scent dispensing hole (e.g., the scent dispensing hole 82).

More specifically, in a further embodiment, the positions of the chambers are defined with respect to a control position, which may be referred to as a "chamber 0" position. Such a control position may be, but is not limited to, a position of a closed compartment which does not contain a chamber (e.g., the closed compartment 32-1). In such an embodiment, positions of the chambers may be defined relative to this chamberless compartment. Defining positions of the chambers relative to a base or control position allows for deterministically identifying where the chambers are in order to aid in dispensing after a user reallocates chambers.

At S1230, a scent dispensing command is received. The scent dispensing command may indicate a scent or combination of scents (e.g., a combination expressed as a combination of different predetermined types of scent essence fluids which may be disposed in the chambers) to be dispensed. The scent dispensing command may be received from a user device or other system through which scents are selected.

In an embodiment, a scanner which scans each machine-readable marker receives data indicating at least which type of scent essence fluid is disposed in the respective chamber of each machine-readable marker. In another embodiment, a scanner which scans each machine-readable marker receives data indicating an identifier of the respective chamber of each machine-readable marker. Such identifiers may be used to determine which scent is disposed in each chamber when a user or other operator of the scent dispensing device refills or otherwise fills one or more of the chambers. For example, data indicating a predetermined type of scent essence which has been used to fill certain chambers may be received along with data indicating the identifiers of the chambers which have been filled this way, and by scanning the machine-readable markers in order to determine an identifier of the chamber disposed in each compartment within the drum, it may therefore be determined which type of scent essence fluid is disposed in each chamber in the drum.

At S1230, available scents are determined. In an embodiment, determining the available scents includes determining a type of scent essence fluid disposed in each chamber currently disposed in the drum, an amount or level of scent essence fluid in each chamber currently disposed in the drum, or both.

As noted above, the types of scent essence fluid disposed in each chamber may be determined based on the scanning of the machine-readable markers, either directly (i.e., by scanning in order to obtain data explicitly indicating the type of scent essence in each chamber) or indirectly (i.e., by scanning in order to obtain data identifying each chamber which, in combination with data indicating a type of scent essence fluid disposed in each chamber identified in the same manner, allows for determining which scent essence is available in each chamber.

The amount or level of scent essence fluid in each chamber may be determined based on an amount of scent essence fluid ejected from each chamber during a last scent dispensing and a previous chamber status of each chamber (e.g., a status indicating an amount of scent essence fluid in the chamber prior to the last scent dispensing). Alternatively, the amount or level of scent essence fluid may be determined by reading an amount of fluid in each chamber relative to a level marker, a weight of each chamber, and the like.

At optional S1240, a notification is sent. The notification indicates whether the received scent dispensing command is feasible. To this end, in an embodiment, S1240 may further include determining required scent essences, required amounts of respective scent essences, or both, needed to perform scent dispensing in accordance with the received scent dispensing command. Such scent essence requirements (i.e., required types and/or amounts of scent essences) may be compared to the scent availability data discussed above with respect to S1230 in order to determine whether the chambers include chambers with each required scent essence, with a required amount of each scent essence, or both.

At S1260, the drum is rotated in order to enable dispensing of the scent or scents indicated in the received scent dispensing command such that an applicable chamber is aligned with an opening of the scent dispensing device or otherwise such that scent essence fluid ejected from the chamber is also ejected from the scent dispensing device, thereby causing dispensing of that scent.

At S1270, scents are caused to be dispensed. In an embodiment, causing scent dispensing includes ejecting scent essence fluid from one or more of the chambers. In a further embodiment, the scent essence fluid is ejected from one or more openings in the scent dispensing device. In yet a further embodiment, causing scents to be dispensed includes activating a motor connected to one or more actuators in each chamber from which scent essence fluid will be ejected, thereby causing the actuator to move in order to effectuate ejection of the scent essence fluid.

In some embodiments, multiple scents may be dispensed. To this end, in such embodiments, the drum may be rotated, and scents may be dispensed iteratively, with the drum being rotated to a respective position and a scent being dispensed from a respective chamber at each iteration. Consequently, in some embodiments, execution may continue with S1250 after at least some iterations of causing scent dispensing at S1260.

At S1280, a chamber status of one or more chambers is updated based on the scent dispensing. In an embodiment, updating the chamber status includes updating an amount or level of scent fluid for each chamber from which a scent was dispensed based on the amount of scent essence fluid which was ejected from the chamber. In another embodiment, updating the chamber status includes updating an amount or level of scent fluid for each chamber from which a scent was dispensed based on a new level of scent essence fluid in each chamber. To this end, in a further embodiment, updating the chamber status further includes reading a level of fluid in each chamber that was used to dispense a scent or otherwise reading fluid levels of chambers in the drum.

FIG. 13 is a schematic diagram of a hardware layer 1300 of a system configured to control scent dispensing of a modular scent dispenser according to an embodiment. The hardware layer 1300 includes a processing circuitry 1310 coupled to a memory 1320, a storage 1330, an interface 1340, and a motor controller 1350. In an embodiment, the components of the hardware layer 1300 may be communicatively connected via a bus 1360. The hardware layer 1300 may be realized at least partially via one or more circuits such as, but not limited to, a circuit incorporated into a printed circuit board such as the PCB 89, FIG. 11.

The processing circuitry 1310 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 1320 may be volatile (e.g., random access memory, etc.), non-volatile (e.g., read only memory, flash memory, etc.), or a combination thereof.

In one configuration, software for implementing one or more embodiments disclosed herein may be stored in the storage 1330. In another configuration, the memory 1320 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 1310, cause the processing circuitry 1310 to perform the various processes described herein.

The storage 1330 may be magnetic storage, optical storage, and the like, and may be realized, for example, as flash memory or other memory technology, compact disk-read only memory (CD-ROM), Digital Versatile Disks (DVDs), or any other medium which can be used to store the desired information.

The interface 1340 allows the hardware layer 1300 to communicate with, for example, one or more networks (not shown). As a non-limiting example, the interface 1340 may be utilized to communicate with a user device or other system (also not shown) in order to receive data such as, but not limited to, data indicating scents to be dispensed, data indicating content (e.g., text, images, audio, etc.) to be projected via a display (not shown) of the scent dispensing device, and the like.

The motor controller 1350 is configured to control one or more motors of a scent dispenser such as, but not limited to, motors configured to move actuators in order to cause scents to be dispensed as described herein, motors configured to rotate a drum as described herein, both, and the like. As a non-limiting example, the motor controller 1350 may control a motor such as the motor 85, FIG. 10.

It should be understood that the embodiments described herein are not limited to the specific architecture illustrated in FIG. 13, and other architectures may be equally used without departing from the scope of the disclosed embodiments.

FIG. 14 is an example top perspective view 1400 of the chamber 10 according to an embodiment. As shown in FIG. 14, the chamber 10 has a casing composed of a first bottom portion 12 and a second top portion 13. The top portion 13 further includes a nozzle 14, an actuator 15, and a valve 16.

As depicted in FIG. 14, the actuator 15 has a fin 21 which is disposed in a slot 22 defined in the top portion 13. The fin 21 may be used to at least partially lock the actuator 15 in place. Specifically, in an embodiment, the fin 21 is disposed in the slot 22 so as to prevent rotation of the actuator 15, i.e., because the fin 21 becomes blocked from moving outside of the slot 22. Accordingly, the fin 21 and slot 22 allow for ensuring that the actuator 15 remains facing forward in order to ensure that the spray nozzle 14 becomes aligned with a scent dispensing hole (such as, but not limited to, the scent dispensing hole 82).

In this regard, it is noted that the actuator 15 may rotate such that the spray nozzle 14 becomes blocked. In particular, it has been identified that such rotation of the actuator 15 may occur when the chamber 10 is inserted into a drum (e.g., the drum 30) or as the drum rotates. The fin 21 may therefore be utilized to prevent such rotation, thereby ensuring that the nozzle 14 does not become blocked and can be used to spray fluid.

FIG. 15 is an example bottom perspective view 1500 of the chamber 10 according to an embodiment. As shown in FIG. 15, the chamber 10 further has a depression 18 into which a machine-readable marker such as a NFC tag may be inserted for use as described herein. The chamber 10 further includes a snap member 19 which may be utilized to lock the chamber 10 into place, for example with a tray of a drum 30 as discussed above.

FIG. 16 is an example front view 1600 of the chamber 10 according to an embodiment. As shown in FIG. 16, the chamber 10 includes the casing featuring the bottom portion 12 and the top portion 13, the nozzle 14, and the actuator 15.

FIG. 17 is an example top view 1700 of the chamber 10 according to an embodiment. As shown in FIG. 17, the top portion 13 of the chamber 10 further includes the actuator 15 and the valve 16. Moreover, the actuator 15 has a fin 21 disposed in a slot 22 of the chamber 10.

FIG. 18 is an example perspective view 1800 of the drum 30 according to an embodiment. As shown in FIG. 18, the drum 30 has separating members 31, compartments 32, scanning apertures 33, and locking apertures 34.

FIG. 19 is an example perspective view 1900 of the chamber 60 having curved upper walls according to an embodiment. As shown in FIG. 19, the chamber 60 has a top portion 61 including side walls 62 and 63, specifically, a first curved side wall 62, and a second curved side wall 63, as well as an actuator 64. As noted above, the curved side walls 62 and 63 may be utilized to improve grip when removing or inserting the chamber 60. Additionally, the actuator 64 has a fin 65 which is disposed in a slot 66 defined in the top portion 61.

FIG. 20 is an example top view 2000 of the chamber 60 according to an embodiment. FIG. 20 depicts the first curved side wall 62 and the second curved side wall 63 of the chamber 60. Additionally, FIG. 20 illustrates the actuator 64 having the fin 65, which in turn is disposed in the slot 66.

FIG. 21 is an example illustration of a mechanism 2100 for causing actuators to move which may be utilized in accordance with various disclosed embodiments. The mechanism 2100 shown in FIG. 21 includes a rotating motor 211, a shaft 212, a push member 213, and a hinged member 214. The mechanism 2100 may be utilized to dispense scents as described herein, more specifically, by causing the rotating motor 211 to rotate in response to a request for scent dispensing.

To this end, rotation of the rotating motor 211 may cause the shaft 212 to raise the push member 213. For example, the shaft 212 may be realized as a rotating exciter such that, when the shaft 212 is rotated, one or more raised portions of the shaft 212 exert upward force on the push member 213. In turn, the push member 213 is raised and pushes against the hinged member 214, causing a protruding left end 215 of the hinged member 214 to move downward. When a chamber 217 is disposed below the hinged member 214 as shown in FIG. 21, this downward movement of the protruding left end 215 causes the protruding left end 215 to exert downward force on an actuator 216 of a chamber 217, thereby causing the actuator to spray scent essence fluid from within the chamber 217.

In some implementations, some or all of the components 211, 212, 213, and 214 of the mechanism 2100 may be affixed or otherwise attached to a housing (e.g., the housing 81) and, more specifically, to a top surface of an interior (not shown) of the housing 81.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

At least some of the embodiments disclosed herein can be implemented as hardware, firmware, software, or any combination thereof. Moreover, the software may be implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. An assembly, comprising:
   a housing;
   a platform disposed in the housing;
   a drum disposed on the platform, the drum having a tray defining a plurality of compartments, wherein at least one first compartment of the plurality of compartments is adapted to receive a respective chamber of a plurality of chambers;
   a first motor, wherein the first motor is connected to the platform;
   a second motor, wherein the second motor is adapted to connect to a plurality of actuators of the plurality of chambers, wherein each chamber of the plurality of chambers defines a cavity, wherein each chamber of the plurality of chambers includes a nozzle connected to a pump, wherein the pump of each chamber includes one of the plurality of actuators and is in fluid connection with the cavity of the chamber, wherein each actuator of the plurality of actuators has a corresponding actuator port; and a controller communicatively connected to the motor, the controller including a processing circuitry and a memory, wherein the controller is configured to provide a first set of input signals to the first motor in order to cause the first motor to engage the drum, wherein the platform rotates when engaged by the first motor, wherein the controller is further configured to provide a second set of input signals to the second motor in order to cause the second motor to engage actuators among the plurality of actuators, wherein the second motor causes the actuator of a first chamber of the plurality of chambers to move in order to exert force on the fluid in the cavity defined in the first chamber, wherein the exertion of force on the fluid in the cavity defined in the first chamber causes the fluid to be ejected via the actuator port of the actuator and through the pump and nozzle.

2. The assembly of claim 1, further comprising:

the plurality of chambers, wherein each chamber of the plurality of chambers is disposed in a compartment of the plurality of compartments, wherein each chamber of the plurality of chambers includes a casing defining the cavity of the chamber adapted to store a respective fluid of a plurality of fluids.

3. The assembly of claim 2, wherein fluid in the cavity of each chamber is ejected from the cavity and exits the chamber through the nozzle of the chamber when the force is exerted on the fluid in the cavity of the chamber.

4. The assembly of claim 3, wherein the pump of each chamber includes a respective actuator of the plurality of actuators that is in fluid connection with the cavity of the chamber such that movement by the actuator of the pump of the chamber exerts force on the fluid in the cavity of the chamber.

5. The assembly of claim 4, wherein the actuator of the pump of each chamber has a top portion defining a slot and a fin disposed in the slot defined in the top portion.

6. The assembly of claim 2, wherein each chamber of the plurality of chambers further includes a valve, wherein the valve of each chamber is fluidly connected to the cavity of the chamber.

7. The assembly of claim 2, wherein the tray defines a plurality of holes, wherein the casing of each cavity further includes a snap member, wherein the snap member of each chamber is configured to lock into one of the plurality of holes of the tray in order to lock the chamber in place within the tray.

8. The assembly of claim 2, wherein each chamber has a machine-readable marker disposed thereon, further comprising:

a scanner, wherein the scanner is configured to scan the machine-readable marker disposed on each chamber, wherein the controller is further configured to determine a scent essence of each chamber by scanning the machine-readable marker disposed on the chamber.

9. The assembly of claim 2, wherein the casing of each chamber defines a depression adapted to receive a machine-readable marker of a plurality of machine-readable markers, further comprising:

a scanner, wherein the scanner is configured to scan the plurality of machine-readable markers, wherein the controller is further configured to determine a scent essence of each chamber by scanning the plurality of machine-readable markers.

10. The assembly of claim 2, wherein the casing of each chamber further includes a first portion and a second portion, wherein the cavity of each chamber is defined in the first portion of the chamber, wherein the first portion of each chamber has a top side, wherein the second portion of each chamber extends from the top side of the first portion of the chamber.

11. The assembly of claim 10, wherein the second portion of the casing of each chamber has a first curved wall and a second curved wall.

12. The assembly of claim 2, wherein the housing defines an aperture, wherein the controller is further configured to:

cause rotation of the tray until a first chamber of the plurality of chambers is aligned with the aperture of the housing; and cause fluid to be dispensed from the first chamber through the aperture of the housing by providing the input signals to the motor when the first chamber is aligned with the aperture of the housing.

13. The assembly of claim 1, wherein the plurality of compartments includes the at least one first compartment and a second compartment, wherein each of the at least one first compartment has a bottom end defining at least one aperture, wherein the second compartment has a bottom end which lacks an aperture.

14. The assembly of claim 13, wherein the second compartment has a machine-readable marker disposed thereon, further comprising:

a scanner, wherein the scanner is configured to scan the machine-readable marker disposed on the second compartment, wherein the controller is further configured to determine a type of the drum by scanning the machine-readable marker disposed on the second compartment.

15. The assembly of claim 1, wherein the plurality of compartments includes the at least one first compartment and a second compartment, the second compartment has a set of side walls and at least one rib, wherein each rib is disposed on one of the side walls of the set of side walls.

16. A method for dispensing scents, comprising:

causing a drum to rotate until a first chamber of a plurality of chambers is aligned with an aperture defined in a housing by providing a first set of input signals to a first motor of an assembly; wherein the assembly includes a housing defining the aperture, a platform disposed in the housing, a drum disposed on the platform, the first motor, a second motor, and the plurality of chambers; wherein the drum has a tray defining a plurality of compartments; wherein each chamber of the plurality of chambers is disposed in a compartment of the plurality of compartments; wherein each chamber of the plurality of chambers includes a casing defining a cavity adapted to store a respective fluid of a plurality of fluids; wherein each chamber of the plurality of chambers further includes a nozzle connected to a pump; wherein the pump of each chamber includes a respective actuator of a plurality of actuators; wherein the pump of each chamber is in fluid connection with the cavity of the chamber; wherein each actuator of the plurality of actuators has a corresponding actuator port; and causing the actuator of the pump of the first chamber of the plurality of chambers to exert force on the pump of the first chamber when the first chamber is aligned with the aperture defined in the housing by providing a second set of input signals to the second motor; wherein the second motor is connected to the plurality of actuators of the plurality of chambers; wherein fluid in the cavity of each chamber is ejected from the cavity and exits the chamber through the nozzle of the chamber when force is exerted on the fluid in the cavity of the chamber, wherein the second motor causes the actuator of a first chamber of the plurality of chambers to move in order to exert force on the fluid in the cavity defined in the first chamber, wherein the exertion of force on the fluid in the cavity defined in the first chamber causes the fluid to be ejected via the actuator port of the actuator and through the pump and nozzle.

17. A non-transitory computer-readable medium having stored thereon instructions for causing a processing circuitry to execute a process, the process comprising:

causing a drum to rotate until a first chamber of a plurality of chambers is aligned with an aperture defined in a housing by providing a first set of input signals to a first motor of an assembly; wherein the assembly includes a housing defining the aperture, a platform disposed in the housing, a drum disposed on the platform, the first motor, a second motor, and the plurality of chambers; wherein the drum has a tray defining a plurality of compartments; wherein each chamber of the plurality of chambers is disposed in a compartment of the plurality of compartments; wherein each chamber of the plurality of chambers includes a casing defining a cavity adapted to store a respective fluid of a plurality of fluids; wherein each chamber of the plurality of chambers further includes a nozzle connected to a pump; wherein the pump of each chamber includes a respective actuator of a plurality of actuators; wherein the pump of each chamber is in fluid connection with the cavity of the chamber; wherein each actuator of the plurality of actuators has a corresponding actuator port; and causing the actuator of the pump of the first chamber of the plurality of chambers to exert force on the pump of the first chamber when the first chamber is aligned with the aperture defined in the housing by providing a second set of input signals to the second motor; wherein the second motor is connected to the plurality of actuators of the plurality of chambers; wherein fluid in the cavity of each chamber is ejected from the cavity and exits the chamber through the nozzle of the chamber when force is exerted on the fluid in the cavity of the chamber, wherein the second motor causes the actuator of a first chamber of the plurality of chambers to move in order to exert force on the fluid in the cavity defined in the first chamber, wherein the exertion of force on the fluid in the cavity defined in the first chamber causes the fluid to be ejected via the actuator port of the actuator and through the pump and nozzle.

\* \* \* \* \*